(12) United States Patent
Iatrou et al.

(10) Patent No.: US 9,615,585 B2
(45) Date of Patent: Apr. 11, 2017

(54) METHODS COMPOUNDS AND COMPOSITIONS FOR REPELLING INSECTS AND/OR ARACHNIDS

(71) Applicant: National Center for Scientific Research "Demokritos", Aghia Paraskevi, Attikis (GR)

(72) Inventors: Kostas Iatrou, Holargos (GR); Patrick Guerin, Fleurier (CH); Thomas Kröber, Neuchatel (CH); Maria Konstantopoulou, Athens (GR)

(73) Assignee: National Centre for Scientific Research-Demokritos, Athens (GR)

( * ) Notice: Subject to any disclaimer, the term of this patent is extended or adjusted under 35 U.S.C. 154(b) by 60 days.

(21) Appl. No.: 14/776,330

(22) PCT Filed: Mar. 14, 2014

(86) PCT No.: PCT/EP2014/055170
§ 371 (c)(1),
(2) Date: Sep. 14, 2015

(87) PCT Pub. No.: WO2014/140314
PCT Pub. Date: Sep. 18, 2014

(65) Prior Publication Data
US 2016/0029643 A1    Feb. 4, 2016

Related U.S. Application Data

(60) Provisional application No. 61/783,955, filed on Mar. 14, 2013.

(51) Int. Cl.
| | | |
|---|---|---|
| *A01N 65/00* | (2009.01) | |
| *A01N 65/22* | (2009.01) | |
| *A01N 31/04* | (2006.01) | |
| *A01N 31/08* | (2006.01) | |
| *A01N 35/04* | (2006.01) | |
| *A01N 37/02* | (2006.01) | |
| *A01N 37/06* | (2006.01) | |
| *A01N 37/10* | (2006.01) | |
| *A01N 31/00* | (2006.01) | |
| *A01N 65/10* | (2009.01) | |
| *G01N 33/566* | (2006.01) | |
| *A61K 36/53* | (2006.01) | |

(52) U.S. Cl.
CPC ............. *A01N 65/22* (2013.01); *A01N 31/00* (2013.01); *A01N 31/04* (2013.01); *A01N 31/08* (2013.01); *A01N 35/04* (2013.01); *A01N 37/02* (2013.01); *A01N 37/06* (2013.01); *A01N 37/10* (2013.01); *A01N 65/00* (2013.01); *A01N 65/10* (2013.01); *G01N 33/566* (2013.01); *A61K 36/53* (2013.01); *G01N 2333/43591* (2013.01)

(58) Field of Classification Search
CPC ...................................................... A61K 36/00
USPC ............................................................ 424/725
See application file for complete search history.

(56) References Cited

U.S. PATENT DOCUMENTS

| | | |
|---|---|---|
| 6,106,838 A | 8/2000 | Nitsas |
| 6,482,455 B1 | 11/2002 | Freire et al. |
| 8,202,557 B1 | 6/2012 | Doty |
| 2003/0175369 A1 | 9/2003 | Khazan-Enache |
| 2005/0008714 A1 | 1/2005 | Enan |
| 2008/0187607 A1 | 8/2008 | Bessette |
| 2009/0155394 A1 | 6/2009 | Overman |
| 2011/0135764 A1 | 6/2011 | Enan |

FOREIGN PATENT DOCUMENTS

| | | |
|---|---|---|
| EP | 2047749 A2 | 4/2009 |
| WO | 2008155536 A1 | 12/2008 |

OTHER PUBLICATIONS

Campbell et al. Forty-two compounds in eleven essential oils elicit antennal responses from Aedes aegypti, Entomologia Experimentalis el Applicata, vol. 138, No. 1, 28 Nov. 2010.
International Search Report, PCT/EP2014/055170, mailed Mar. 3, 2015.
Morteza-Semnani Essential Oil Composition of Eryngium bungei Boiss, Journal of Essential Oil Research, vol. 17, No. 5, Sep. 1, 2005.
Steketee et al. Impact of national malaria control scale-up programmes in Africa: magnitude and attribution of effects, Malaria Journal, Biomed Central, London, GB, vol. 9, No. 1, Oct. 27, 2010.
Written Opinion PCT/EP2014/055170, Apr. 8, 2015.
Yang et al. Study of Volatile Chemical Constituents in Different Parts of Picrasma quassioides, Chinese Journal of Experimental Traditional Medical Formulae, May 1, 2011 retrieved from the Internet: http://en.cnki.com.cn/Article_en/CJFDTOTAL-ZSFX201105029.htm (Abstract).

*Primary Examiner* — Michael Meller
(74) *Attorney, Agent, or Firm* — One3 IP Management, P.C.; Dean G. Stathakis; Peter D. Weinstein

(57) ABSTRACT

The present specification discloses natural repellent compounds, and isomeric forms, structural analogs and derivatives of the said compounds, having repellent activity against mosquitoes and other blood-sucking arthropods, compositions comprising such repellent compounds, methods of screening for such repellent compounds, methods of reducing mosquito bites on an individual and methods of reducing mosquito infestation to a location.

20 Claims, 4 Drawing Sheets

```
                          SEQUENCE LISTING

<160> NUMBER OF SEQ ID NOS: 13

<210> SEQ ID NO 1
<211> LENGTH: 127
<212> TYPE: PRT
<213> ORGANISM: Anopheles gambiae

<400> SEQUENCE: 1

Trp Gly Asp Thr Thr Pro Arg Arg Asp Ala Glu Tyr Pro Pro Pro Glu
1               5                   10                  15

Leu Leu Glu Ala Leu Lys Pro Leu His Asp Ile Cys Leu Gly Lys Thr
            20                  25                  30

Gly Val Thr Glu Glu Ala Ile Lys Lys Phe Ser Asp Glu Glu Ile His
        35                  40                  45

Glu Asp Glu Lys Leu Lys Cys Tyr Met Asn Cys Leu Phe His Glu Ala
    50                  55                  60

Lys Val Val Asp Asp Asn Gly Asp Val His Leu Glu Lys Leu His Asp
65                  70                  75                  80

Ser Leu Pro Ser Ser Met His Asp Ile Ala Met His Met Gly Lys Arg
                85                  90                  95

Cys Leu Tyr Pro Glu Gly Glu Thr Leu Cys Asp Lys Ala Phe Trp Leu
            100                 105                 110

His Lys Cys Trp Lys Gln Ser Asp Pro Lys His Tyr Phe Leu Val
        115                 120                 125

<210> SEQ ID NO 2
<211> LENGTH: 132
<212> TYPE: PRT
<213> ORGANISM: Anopheles gambiae

<400> SEQUENCE: 2

Ser Thr Ile Thr Thr Gln Arg Pro Ala Pro Arg Arg Asp Gly Gln Tyr
1               5                   10                  15

Pro Pro Pro Glu Thr Leu Ala Phe Leu Arg Pro Leu Gly Lys Leu Cys
            20                  25                  30

Leu Glu Glu Thr Gly Val Ser Pro Glu Ala Ile Lys Arg Phe Ser Asp
        35                  40                  45

Ala Asp Pro Phe Asp Asp Asn Arg Ala Leu Lys Cys Tyr Met Asp Cys
    50                  55                  60

Met Phe Arg Val Thr Asn Val Thr Asp Asp Arg Gly Glu Leu His Met
65                  70                  75                  80

Gly Lys Leu Leu Glu His Val Pro Thr Glu Phe Glu Asp Ile Ala Leu
```

```
                    85                  90                  95

Arg Met Gly Val Arg Cys Thr Arg Pro Lys Gly Lys Asp Val Cys Glu
            100                 105                 110

Arg Ala Phe Trp Phe His Lys Cys Trp Lys Thr Ser Asp Pro Val His
            115                 120                 125

Tyr Tyr Leu Val
        130

<210> SEQ ID NO 3
<211> LENGTH: 125
<212> TYPE: PRT
<213> ORGANISM: Anopheles gambiae

<400> SEQUENCE: 3

Gly Asp Glu Pro Arg Arg Asp Ala Asn Tyr Pro Pro Glu Leu Leu
1               5                   10                  15

Glu Lys Met Lys Pro Met His Asp Ala Cys Val Ala Glu Thr Gly Ala
            20                  25                  30

Ser Glu Asp Ala Ile Lys Arg Phe Ser Asp Gln Glu Ile His Glu Asp
        35                  40                  45

Asp Lys Leu Lys Cys Tyr Met Asn Cys Leu Phe His Gln Ala Gly Val
    50                  55                  60

Val Asn Asp Lys Gly Glu Phe His Tyr Val Lys Ile Gln Asp Phe Leu
65                  70                  75                  80

Pro Glu Ser Met His Leu Ile Thr Leu Asn Trp Phe Lys Arg Cys Leu
                85                  90                  95

Tyr Pro Glu Gly Glu Asn Gly Cys Glu Lys Ala Phe Trp Leu Asn Lys
            100                 105                 110

Cys Trp Lys Thr Arg Asp Pro Val His Tyr Phe Leu Pro
            115                 120                 125

<210> SEQ ID NO 4
<211> LENGTH: 125
<212> TYPE: PRT
<213> ORGANISM: Anopheles gambiae

<400> SEQUENCE: 4

Ala Met Thr Met Lys Gln Leu Thr Asn Ser Met Asp Met Met Arg Gln
1               5                   10                  15

Ala Cys Ala Pro Lys Phe Lys Val Glu Glu Ala Glu Leu His Gly Leu
            20                  25                  30

Arg Lys Ser Ile Phe Pro Ala Asn Pro Asp Lys Glu Leu Lys Cys Tyr
        35                  40                  45

Ala Met Cys Ile Ala Gln Met Ala Gly Thr Met Thr Lys Lys Gly Glu
    50                  55                  60

Ile Ser Phe Ser Lys Thr Met Ala Gln Ile Glu Ala Met Leu Pro Pro
65                  70                  75                  80

Glu Met Lys Thr Met Ala Lys Glu Ala Leu Thr His Cys Lys Asp Thr
                85                  90                  95

Gln Thr Ser Tyr Lys Asp Pro Cys Asp Lys Ala Tyr Phe Ser Ala Lys
            100                 105                 110

Cys Ala Ala Asp Phe Thr Pro Asp Thr Phe Met Phe Pro
            115                 120                 125

<210> SEQ ID NO 5
<211> LENGTH: 123
<212> TYPE: PRT
```

-continued

<213> ORGANISM: Anopheles gambiae

<400> SEQUENCE: 5

Ala Met Thr Arg Lys Gln Leu Ile Asn Ser Met Asp Met Arg Ser
1               5                   10                  15

Ala Cys Ala Pro Lys Phe Lys Val Ser Thr Glu Met Leu Asp Asn Leu
            20                  25                  30

Arg Gly Gly Ile Phe Ala Glu Asp Arg Glu Leu Lys Cys Tyr Thr Met
        35                  40                  45

Cys Ile Ala Gln Met Ala Gly Thr Met Asn Lys Lys Gly Glu Ile Asn
    50                  55                  60

Val Pro Lys Thr Leu Ala Gln Met Asp Ala Met Leu Pro Pro Asp Met
65                  70                  75                  80

Arg Asp Lys Ala Lys Glu Ala Ile His Ser Cys Arg Asp Val Gln Gly
                85                  90                  95

Arg Tyr Lys Asp Ser Cys Asp Lys Thr Phe Tyr Ser Thr Lys Cys Leu
            100                 105                 110

Ala Glu Tyr Asp Arg Asp Val Phe Leu Phe Pro
        115                 120

<210> SEQ ID NO 6
<211> LENGTH: 122
<212> TYPE: PRT
<213> ORGANISM: Anopheles gambiae

<400> SEQUENCE: 6

Gln Gln Ser Leu Thr Gln Ala Asp Met Asp Glu Ile Ala Lys Gly Met
1               5                   10                  15

Arg Lys Val Cys Met Ser Arg His Lys Ile Ser Glu Glu Met Ala Asn
            20                  25                  30

Tyr Pro Ser Gln Gly Ile Phe Pro Asp Asp Gln Glu Phe Lys Cys Tyr
        35                  40                  45

Val Ala Cys Leu Met Asp Leu Thr Gln Thr Ser Lys Lys Gly Lys Leu
    50                  55                  60

Asn Tyr Asp Ala Ala Val Lys Gln Ile Asp Ile Leu Pro Glu Asn Tyr
65                  70                  75                  80

Arg Gln Pro Phe Arg Leu Gly Leu Asp Ser Cys Arg Thr Ala Ala Asp
                85                  90                  95

Asp Ala Thr Asp Arg Cys Glu Val Ala Tyr Ile Leu Leu Lys Cys Phe
            100                 105                 110

Phe Lys Ala Ser Pro Lys Phe Phe Pro
        115                 120

<210> SEQ ID NO 7
<211> LENGTH: 126
<212> TYPE: PRT
<213> ORGANISM: Anopheles gambiae

<400> SEQUENCE: 7

Ala Pro Phe Glu Ile Pro Asp Arg Tyr Lys Lys Pro Ala Lys Met Leu
1               5                   10                  15

His Glu Ile Cys Ile Ala Glu Ser Gly Ala Ser Glu Glu Gln Leu Arg
            20                  25                  30

Thr Cys Leu Asp Gly Thr Val Pro Thr Ala Pro Ala Lys Cys Tyr
        35                  40                  45

Ile His Cys Leu Phe Asp Lys Ile Asp Val Val Asp Glu Ala Thr Gly
    50                  55                  60

```
Arg Ile Leu Leu Asp Arg Leu Leu Tyr Ile Ile Pro Asp Asp Val Lys
 65                  70                  75                  80

Ala Ala Val Asp His Leu Thr Arg Glu Cys Ser His Ile Val Thr Pro
                 85                  90                  95

Asp Lys Cys Glu Thr Ala Tyr Glu Thr Val Lys Cys Tyr Phe Asn Ala
            100                 105                 110

His Asp Glu Val Ile Lys Phe Cys His Leu Leu Val Leu Glu
        115                 120                 125

<210> SEQ ID NO 8
<211> LENGTH: 122
<212> TYPE: PRT
<213> ORGANISM: Anopheles gambiae

<400> SEQUENCE: 8

Glu Phe Val Val Gln Thr Arg Glu Asp Leu Leu Ala Tyr Arg Ala Glu
 1               5                  10                  15

Cys Val Lys Ser Leu Gly Val Ser Asp Glu Leu Val Glu Lys Tyr Lys
             20                  25                  30

Ser Trp Asn Phe Pro Glu Asp Asp Thr Thr Gln Cys Tyr Ile Lys Cys
         35                  40                  45

Ile Phe Asn Lys Met Gln Leu Phe Asp Asp Thr Asn Gly Pro Ile Val
 50                  55                  60

Asp Asn Leu Val Val Gln Leu Ala His Gly Arg Asp Ala Asn Glu Val
 65                  70                  75                  80

Arg Glu Glu Ile Val Lys Cys Ala Gly Ser Asn Thr Asp Gly Asn Val
                 85                  90                  95

Cys His Trp Ala Phe Arg Gly Phe Gln Cys Phe Gln Lys Asn Asn Leu
            100                 105                 110

Ser Leu Ile Lys Ala Ser Val Lys Lys Asp
        115                 120

<210> SEQ ID NO 9
<211> LENGTH: 132
<212> TYPE: PRT
<213> ORGANISM: Anopheles gambiae

<400> SEQUENCE: 9

Leu Asp Ile Ser Lys Val Thr Leu Asp Ala Ala Phe Tyr Pro Leu Phe
 1               5                  10                  15

Gly Cys Ala Arg Asp Leu Val Val Pro Glu Asp Leu Ile Glu Leu Tyr
             20                  25                  30

Lys Lys Arg Ile Phe Pro Asp Asp Gln Leu Thr Cys Cys Val Phe Arg
         35                  40                  45

Cys Leu Gly Met Arg Leu Gly Ile Tyr Asp Asp Val Lys Gly Phe Asp
 50                  55                  60

Val Asp Lys Gln Tyr Glu Arg Val Lys Asp Arg Leu Ser Val Asp Glu
 65                  70                  75                  80

Asp Thr Tyr Lys Arg Gly Val Lys Asn Cys Ile Arg Asn Val Leu Arg
                 85                  90                  95

Gly Arg Thr Leu Asn Asn Cys Gly Lys Ala Tyr Leu Ile Leu Asn Gln
            100                 105                 110

Cys Gln Gly Asn Thr Ile Thr Asn Ser Leu Asn Gln Gln Leu Asn Glu
        115                 120                 125

Ile Arg Cys Asn
        130
```

<210> SEQ ID NO 10
<211> LENGTH: 166
<212> TYPE: PRT
<213> ORGANISM: Anopheles gambiae

<400> SEQUENCE: 10

```
Lys Lys Ala Ser Thr Ile Phe Gly Met Pro Leu Gln Gln Asp Pro Val
1               5                   10                  15

Pro Ala Thr Ser Thr Phe Ile Val Ser Asp Phe Leu Gln Phe Leu Gln
            20                  25                  30

Thr Ala Val Thr Cys Phe Asn Lys Leu Arg Ile Pro Glu Glu Arg Phe
        35                  40                  45

Pro Leu Tyr Leu Ala Gly Val Phe Pro Asn Cys Pro Glu Thr Gln Cys
    50                  55                  60

Phe Val Arg Cys Leu Ser Ala Asn Leu Asn Leu Tyr Cys Asp Glu Thr
65                  70                  75                  80

Gly Ser Asp Ile Asp Arg His Tyr Leu Gln Tyr Gly Leu Gly Gln Asp
                85                  90                  95

Tyr Asn Cys Phe Arg Gln Lys Ala Glu Gln Cys Leu Ala Ala Asn Thr
            100                 105                 110

Ser Pro Cys Asn Asp Pro Cys Glu Ala Ala Tyr Lys Gln Glu Leu Cys
        115                 120                 125

Phe Leu Asp Glu Phe Arg Lys Tyr Val Asp Ser Asn Met Asn Ser Leu
    130                 135                 140

Ile Ala Ala Val Ala Val Glu Lys Ala Glu Gln Asn Pro Val Tyr Tyr
145                 150                 155                 160

Asn Met Leu Ala His Asn
                165
```

<210> SEQ ID NO 11
<211> LENGTH: 128
<212> TYPE: PRT
<213> ORGANISM: Anopheles gambiae

<400> SEQUENCE: 11

```
Lys Lys Ile Phe Pro Leu Arg Lys Ser Thr Val Glu Gln Met Met Lys
1               5                   10                  15

Ser Gly Glu Met Ile Arg Ser Val Cys Leu Gly Lys Thr Lys Val Ala
            20                  25                  30

Glu Glu Leu Val Asn Gly Leu Arg Glu Ser Lys Phe Ala Asp Val Lys
        35                  40                  45

Glu Leu Lys Cys Tyr Val Asn Cys Val Met Glu Met Met Gln Thr Met
    50                  55                  60

Lys Lys Gly Lys Leu Asn Tyr Asp Ala Ser Val Lys Gln Ile Asp Thr
65                  70                  75                  80

Ile Met Pro Asp Glu Leu Ala Gly Pro Met Arg Ala Ala Leu Asp Ile
                85                  90                  95

Cys Arg Thr Val Ala Asp Gly Ile Lys Asn Asn Cys Asp Ala Ala Tyr
            100                 105                 110

Val Leu Leu Gln Cys Leu Ser Lys Asn Asn Pro Lys Phe Ile Phe Pro
        115                 120                 125
```

<210> SEQ ID NO 12
<211> LENGTH: 175
<212> TYPE: PRT
<213> ORGANISM: Anopheles gambiae

<400> SEQUENCE: 12

```
Gly Asn Pro Cys Leu Lys Gly Pro Val Pro Lys Asn Ala Ala Glu
1               5                   10                  15

Cys Cys Val Thr Pro Phe Leu Val Glu Pro Ser Ala Phe Met Thr Cys
            20                  25                  30

His Ser Lys Trp Ile Gly Gln Thr Lys Arg Gln Met Ala Met Glu Gly
            35                  40                  45

Ile Pro Arg Gly Cys Cys Val Ala Glu Cys Val Met Asn Ser Thr Ser
        50                  55                  60

Leu Tyr Ser Asn Gly Lys Ile Asp Arg Glu Ala Leu Thr Lys Leu Tyr
65                  70                  75                  80

Leu Asp Ser Thr Lys Ser Met Ala Pro Glu Trp Asn Lys Ile Thr Leu
                85                  90                  95

Asp Ala Ile Asp Gly Cys Phe Lys Met Ala Asp Ser Ile Arg Asp Glu
            100                 105                 110

Ile Glu Ala Gly Ala Lys Leu Thr Pro Ala Phe Asp Gly Glu Gln Ile
        115                 120                 125

Cys His Pro Ile Ser Gly Thr Ile Leu Ala Cys Met Gly Met Thr Leu
130                 135                 140

Phe Ala Glu Cys Pro Ala Lys Leu Phe Thr Val Asn Asp Asp Cys Asn
145                 150                 155                 160

Lys Leu Lys Ser Tyr His Ser Lys Cys Pro Phe Leu Ser Thr Leu
                165                 170                 175
```

<210> SEQ ID NO 13
<211> LENGTH: 171
<212> TYPE: PRT
<213> ORGANISM: Anopheles gambiae

<400> SEQUENCE: 13

```
Asp Asn Pro Cys Ala Ala Gly Pro Pro Val Asp Thr Asn Pro Ala Glu
1               5                   10                  15

Cys Cys Pro Lys Pro Met Leu Val Asp Gly Thr Ile Met Met Asp Cys
            20                  25                  30

Tyr Lys Lys Tyr Gly Glu Gln Thr Lys Lys Gln Leu Gln Met Asp Gly
            35                  40                  45

Ile Pro Arg Gly Cys Cys Ile Ala Glu Cys Ala Met Asn Ala Thr Asn
        50                  55                  60

Met Tyr Ala Asp Gly Met Leu Lys Arg Asp Asp Leu Ser Lys Met Phe
65                  70                  75                  80

Met Asp Ala Val Lys Asp Lys Pro Glu Trp Met Ser Leu Val Arg Asp
                85                  90                  95

Ala Thr Asn Ala Cys Phe Glu Leu Ala Glu Lys Lys Met Asp Glu Ile
            100                 105                 110

Glu Ala Gly Ala Lys Leu Glu Pro Ser Phe Glu Gly Glu Lys Ile Cys
        115                 120                 125

His Pro Ile Ser Gly Thr Ile Leu Arg Cys Met Gly Met Met Met Phe
130                 135                 140

Ala Gln Cys Pro Ala Ser Val Phe Asn Val Asn Glu Asn Cys Asn Lys
145                 150                 155                 160

Leu Arg Glu Tyr Gly Ser Ile Cys Pro Met Ile
                165                 170
```

METHODS COMPOUNDS AND COMPOSITIONS FOR REPELLING INSECTS AND/OR ARACHNIDS

This application is a 35 U.S.C. §371 US national stage entry of International Application PCT/EP2014/055170, filed Mar. 14, 2014, and claims the benefit of priority and is entitled to the filing date of U.S. Provisional Patent Application 61/783,955, filed on Mar. 14, 2013, the contents of each of which are hereby incorporated by reference in its entirety.

TECHNICAL FIELD

The present invention relates to novel compounds and compositions, to insect repellent compounds and compositions, to methods of using the compounds and compositions, to methods of screening and/or identifying compounds and/or compositions for their insect repellent activity.

INTRODUCTION

Mosquito-borne diseases, including malaria, yellow fever, and dengue fever, West Nile virus, Eastern equine encephalitis and other illnesses, are a major threat to over 2 billion people world-wide. Integration of disease treatment with vector suppression is considered the most effective means for disease management. However, strenuous efforts to control such mosquito-borne diseases using this integrated approach over the last 60 years have proven unsuccessful. One reason underlying the ineffectiveness of this approach is the widespread resistance of the parasite to commercially available drugs and the absence of effective vaccines. Another reason involves resistance to the insecticides used in vector control measures and personal protection from mosquito bites. Both the failure of the integrated approach for controlling mosquito-borne diseases and the unavailability of new drugs has led to the exploration of new directions for vector control measures aimed at disease eradication.

The most common mosquito repellents available in the market contain DEET (N,N-diethyl-3-methylbenzamide) or Picaridine (1-piperidinecarboxylic acid 2-(2-hydroxyethyl)-1-methylpropylester). DEET is a broad-spectrum repellent that is effective against mosquitoes and other biting insects. Also a broad-spectrum repellent, Picaridine is a synthetic derivative of piperine, a compound found in plants used to produce black pepper. Despite their effectiveness, both of these synthetic repellents have many drawbacks. Besides its unpleasant odor and poor skin penetration, DEET elicits allergic reactions and is a possible neurotoxin and carcinogen in mammals. In addition, DEET reacts with certain plastics and synthetic materials, resulting in considerable damage to eyeglasses and watchbands, and other plastic items. Picaridine has been associated with both skin and eye irritation. Because of the general public's concern about the safety of these synthetic repellents, there has been increasing need to identify new natural and synthetic compounds having repellent activity similar to DEET and Picaridine, but lacking their undesirable properties.

The present specification discloses such mosquito repellents and uses and methods for identifying such compounds. The disclosed mosquito repellents will benefit current approaches being used to control mosquito-borne diseases.

SUMMARY

The present invention relates to novel compounds and compositions. In an aspect, the invention relates to compounds and compositions for repelling arthropods, in particular insects and arachnids.

Aspects of the present specification disclose repellent compounds that bind to specific chemosensory proteins from the chemosensory signaling pathways used by mosquitoes and affect the behavioral activity of mosquitoes by eliciting an avoidance response. A repellent compound disclosed herein has mosquito repellent activity and may bind at least one of the following mosquito odorant-binding proteins (OBPs): OBP1, OBP3, OBP4, OBP5, OBP20, OBP47 and/or other selected OBPs. The disclosed repellent compounds have a mosquito repellence activity, reduce a mosquito-mammalian host interaction, and/or reduce an ability of a mosquito to obtain a blood meal from a mammal.

Other aspects of the present specification disclose compositions comprising a plurality of repellent compounds disclosed herein. The plurality of repellent compounds includes a carvacrol compound, a cumin compound, a cinnamate compound, or any combination thereof. Compositions disclosed herein may, for example, comprise a carvacrol compound disclosed herein and one or more additional repellent compounds having mosquito repellent activity. The one or more additional repellent compounds include a cumin compound, a cinnamate compound, or any combination thereof. The disclosed compositions have a mosquito repellence activity, reduce mosquito-mammalian host interaction, and/or reduce an ability of a mosquito to obtain a blood meal from a mammal.

Other aspects of the present specification disclose methods of reducing mosquito bites on an individual, the method comprising the step of applying a repellent compound or composition disclosed herein to the individual, wherein application of the repellent compound or composition repels a mosquito from the individual, thereby reducing mosquito bites. Application of the composition may be by direct or indirect administration.

Other aspects of the present specification disclose methods of reducing a mosquito infestation to a location, the method comprising the steps of applying a repellent compound or composition disclosed herein to the location, wherein the application repels mosquitoes from the location, thereby reducing the mosquito infestation. The location may be a plant or group of plants, a particular area of land, or a man-made structure, such as, e.g., a commercial building, a house, a shed, or other physical structure.

In an aspect, the invention provides a composition comprising a combination of two or more essential oils or essential oil fractions or combinations thereof as repellents.

In an aspect, the invention relates to novel compounds and compositions, in particular for repelling terrestrial arthropods.

In an aspect, the invention relates to compounds and compositions that are capable of repelling insects and arachnids that can act as vectors for infectious pathogens.

In an aspect, the invention relates to compounds and compositions for preventing arthropod-borne diseases.

In an aspect, the invention provides a compound of formula (IV) as a repellent of insects and/or arachnids:

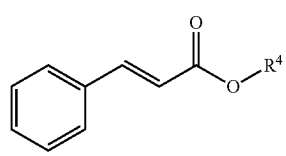

(IV)

wherein $R^4$ is a C2-C10, preferably a C3-C10, most preferably a C4-C10 aliphatic substituent. The invention also relates to methods for repelling insects using and/or applying the compound of formula (IV).

In an aspect, the invention provides a method for screening and/or identifying essential oils having repellent activity with respect to blood-feeding insects and/or arachnid, the method comprising the step of exposing an essential oil or a fraction thereof to be screened to one or more odorant-binding protein (OBP) and determining an binding affinity of said oil or fraction with respect to said OBP, wherein an essential oil or fraction thereof is identified as having insect and/or arachnid repellent activity if it has a binding affinity to said OBP.

BRIEF DESCRIPTION OF THE DRAWINGS

FIGS. 3A and 3B show induced exophily as a measure of repellency of individual chemical compounds on *Anopheles gambiae* s.l. (FIG. 3B), respectively, as compared to DEET, and induced exophily as a measure of repellence of binary combinations of carvacrol with either ethyl-cinnamate, butyl-cinnamate or cumin alcohol on *Anopheles gambaie* s.l. and *Culex* spp. as compared to DEET. The tested compounds are carvacrol (Cary), cumin alcohol (CuAlc), (E)-ethyl-cinnamate (CinEt) and butyl-cinnamate (CinBut). ContMeth is a methanol control.

DESCRIPTION

Figure 1:
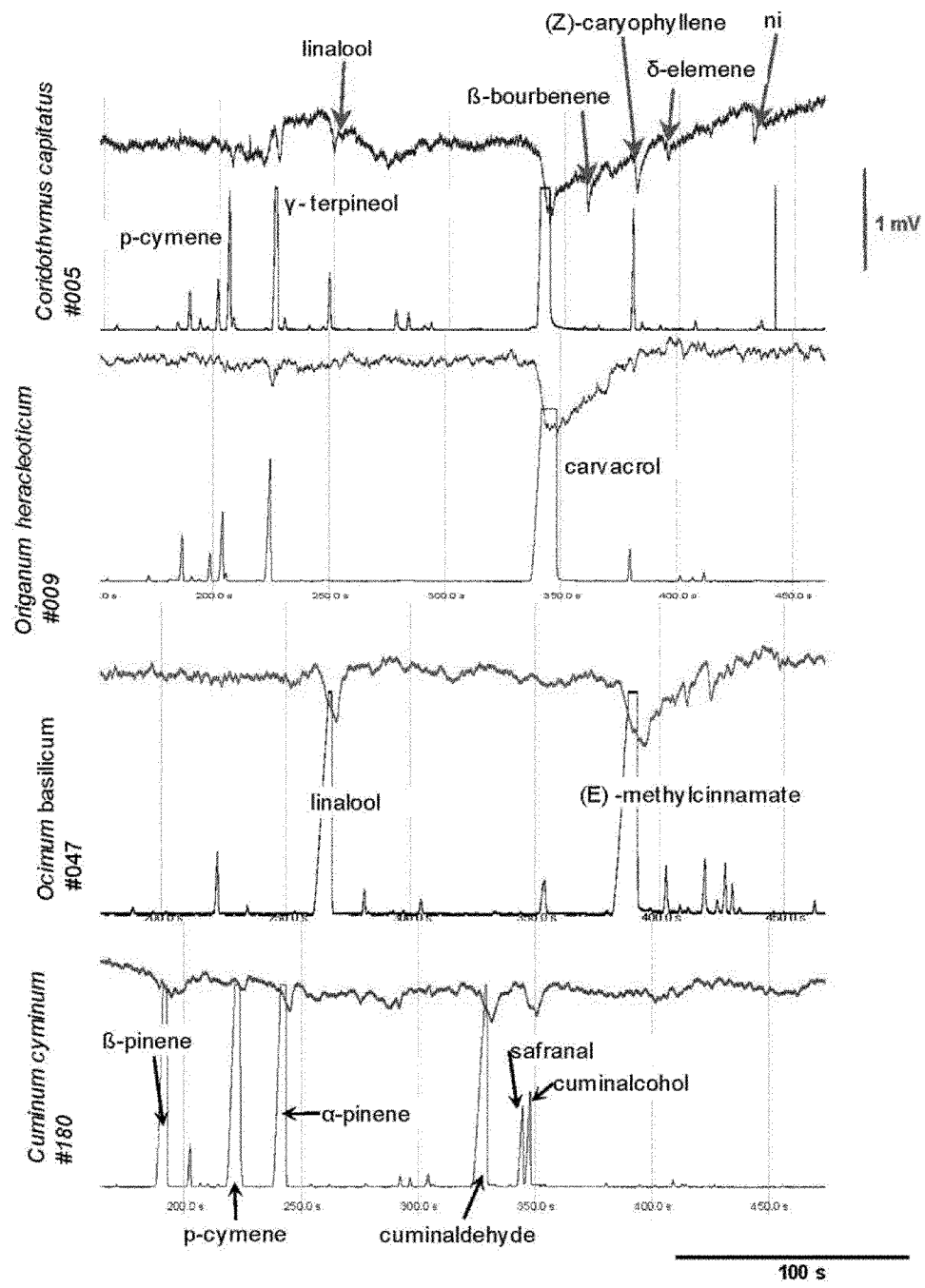
FIG. 1 shows GC-EAG analysis of four selected essential oils that show affinity to OBPs and induce repellence. Some of the identified compounds are indicated in the readouts presented. The female *A. gambiae* antenna was used as a biological detector (upper trace in each case) for active constituents of the essential oils. The lower traces in each case are the flame ionization detector responses.

Insect chemosensory proteins (CSPs) regulate or control crucial insect behaviors. The chemosensory system consists of several chemosensory protein (CSP) classes. Chemosensory protein classes that are important in the design of novel insect control products include soluble proteins found in the antennal sensory lymph and the maxillary palps, such as OBPs and sensory appendage proteins (SAPs). OBPs and SAPs are carrier proteins that facilitate the transport of stimuli from the exterior such as odor molecules through the aqueous lymph of sensory appendages to the surfaces of neuronal cells. There, the protein/odorant molecule complexes bind odorant receptors (ORs) and initiate a signaling cascade that results in a behavioral response to the external odour or stimulus. Insects use chemosensory cues from the environment to control critical behaviors, such as feeding and mating. Thus, insect chemosensory proteins are promising targets for the discovery of novel insect control products based on manipulating insect behavior.

Research on insect repellents has identified various plants as potential sources of essential oils or fumigants that are effective at repelling mosquitoes and other insect pests. These essential oils have a pleasant fragrance, relatively low mammalian toxicity, and a vapor pressure suitable for action as a volatile spatial repellent. Although one or more chemical compounds contained in essential oils are responsible for their repellence, it is not necessarily true that the most abundant compounds are responsible for this activity. In addition, the structures of these compounds cover a very wide diversity of chemical classes and molecular sizes making it difficult to build a consensus rationale relating to the repellent activity for these compounds.

The present specification discloses compositions that are active as repellents of arthropods, in particular terrestrial arthropods, such as insects and arachnids. In an embodiment, the compositions of the invention repel insects and arachnids. In embodiment, the composition of the invention repels blood-feeding arthropods, in particular blood-feeding insects and/or ticks. In a preferred embodiment, the invention relates to repellents of insects and arachnids that act as vectors for a pathogen. In an embodiment, the invention relates to repellents of insects and ticks.

The compositions of the invention have been shown to repel one or more selected from *Anopheles, Aedes*, and *Culex* mosquitos, sand flies and ixodid ticks. The compositions of the invention are suitable to repel one or more selected from *Anopheles gambiae, Aedes aegypti, Lutzomyia longipalpis*, and ixodid ticks, such as *Ixodes ricinus*.

The invention relates to compounds and compositions for preventing infection of insect-borne and/or tick-borne diseases.

The present specification discloses improved mosquito repellents and uses and methods for identifying such repellents. By realizing that repellent compounds could bind to specific chemosensory proteins from the chemosensory signaling pathways used by mosquitoes, effective repellent compounds have been identified and isolated from essential oils. In some embodiments, the compounds are bound by OBPs and show mosquito repellent effects. In addition, the present specification discloses various combinations of these repellent compounds that when combined produce behavioral effects having similar, if not better, repellence to that of DEET. As such, the repellents disclosed herein manipulate the mosquito's chemosensory signalling pathway and affect the behavioral activity of mosquitoes by eliciting an avoidance response. The repellents disclosed herein are intended for agricultural, commercial, and consumer use. For example, the mosquito repellents disclosed herein are useful to repel mosquitoes from areas where humans reside in order to reduce the transmission of mosquito-borne diseases. As another non-limiting example, the mosquito repellents disclosed herein can be applied to humans to reduce or prevent mosquitoes from obtaining a blood-meal from that person. As yet another non-limiting example, the mosquito repellents disclosed herein are useful to keep away mosquitoes from outdoor areas where human activities are occurring and would otherwise be disrupted by mosquito presence, such as, e.g., an outdoor activity like a sporting event or picnic. Similarly, the mosquito repellents disclosed herein are useful to keep away mosquitoes from naturally occurring or man-made structures containing standing water in order to prevent egg-laying and mosquito larva development. Other uses of the mosquito repellents disclosed herein are discussed below and are readily apparent to a person of ordinary skill.

Mosquitoes are insects of the Order Diptera, Superfamily Culicoidea. Comprising a group of about 3,500 species that live throughout the world, mosquitoes are divided into three subfamilies (*Anophelinae, Culicinae*, and *Toxorhynchitinae*) comprising 41 genera including, without limitation, *Anopheles, Aedes*, and *Culex*. Malaria is transmitted by female mosquitoes of the genus *Anopheles*, and of the approximately 430 described species of *Anopheles* over 100 are known to be able to transmit malaria to humans. Yellow and dengue fever are transmitted by female mosquitoes from the genus *Aedes*, while West Nile virus, filariasis, Japanese and St Louis encephalitis and avian malaria are transmitted by female mosquitoes from the genus *Culex*.

Aspects of the present specification disclose, in part a repellent compound. As used herein, the term "repellent compound" is synonymous with "mosquito repellent" refers to a compound that binds to an OBP and/or SAP and induces a behavioral response which causes the insect to move away from the source of the repellent compound and/or reduce or prevent the mosquito's ability to obtain a blood-meal from a mammal. A repellent compound will typically preferentially bind, without limitation, at least one of the following mosquito OBPs: odorant-binding protein 1 (OBP1; SEQ ID NO: 1), odorant-binding protein 3 (OBP3; SEQ ID NO: 2), odorant-binding protein 4 (OBP4; SEQ ID NO: 3), odorant-binding protein 5 (OBP5; SEQ ID NO: 4), odorant-binding protein 20 (OBP20; SEQ ID NO: 5), and/or odorant-binding protein 47 (OBP47; SEQ ID NO: 6). In other embodiments, a repellent compound does not bind to an OBP.

In an aspect, the invention provides a method of screening, preferably prescreening essential oils and/or fractions thereof using an OBP binding assay. This screening or prescreening is an efficient way of reducing the number of samples to be analyzed in subsequent sample analysis and compound identification steps and methods. The present specification contains experimental details with respect to the assessment of the OBP binding affinity of candidate essential oils or fractions thereof.

In some embodiments, the method of the invention comprises the step of exposing a surface mimicking the surface of a mammal to an essential oil and/or fraction thereof or to compositions as disclosed herein and determining a number of landings of said insects and/or, more generally, contacts in the case of arachnids on said surface, wherein an essential oil or fraction thereof or composition as disclosed herein is identified as having insect and/or arachnid repellent activity if it is effective to reduce the number of landings or contacts by said insects and/or arachnids. Similarly, this method can be used preferably together with OBP assay for prescreening or screening agents, compositions or compounds having repellence activity. The surface mimicking the surface of a mammal is preferably a warm surface (30-34° C.). Preferably, the carbon dioxide concentration is increased on the surface. A detailed methodology of such an assay is described in the examples.

Aspects of the present specification disclose, in part a carvacrol compound. Non-limiting examples of suitable carvacrol compounds include, e.g., carvacrol (5-isopropyl-2-methylphenol) and thymol (2-Isopropyl-5-methylphenol).

In an embodiment, a repellent compound is a carvacrol compound or is selected from carvacrol compounds. In another embodiment, a repellent compound is a carvacrol compound having a structure of formula I:

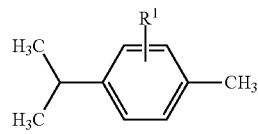

wherein $R^1$ is H, OH, =O, a halogen, or an optionally substituted alkyl, an alkoxy. In aspects of this embodiment, an optionally substituted alkyl is an optionally substituted $C_{1-6}$ alkyl. In other aspects of this embodiment, a halogen is F, Cl, Br, or I. In aspects of this embodiment, an alkoxy is —$OCH_3$, —$OC_2H_5$, —$OC_3H_7$, or —$OC_4H_9$.

As used herein the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In aspects of this embodiment, alkyl may include $C_{1-10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.) $C_6H_{11}$ (e.g. cyclohexyl isomers), $C_7H_{13}$ (e.g. cycloheptyl isomers), etc.; and the like.

With respect to an optionally substituted moiety such as optionally substituted alkyl, a phrase such as "optionally substituted alkyl" refers to an alkyl that may be unsubstituted, or may have one or more substituents, and does not limit the number of carbon atoms in any substituent. A phrase such as "$C_{1-12}$ optionally substituted alkyl" refers to unsubstituted $C_{1-12}$ alkyl, or substituted alkyl wherein both the alkyl parent and all substituents have from 1-12 carbon atoms. Similar conventions may be applied to other optionally substituted moieties such as aryl and heteroaryl.

Substituents on alkyl may be the same as those described generally above, except that alkyl may not have an alkyl substituent. In some embodiments, substituents on alkyl are independently selected from F, Cl, Br, I, OH, NH, =O, etc.

As used herein, the term "alkoxy" includes —O-alkyl, such as —$OCH_3$, —$OC_2H_5$, —$OC_3H_7$ (e.g. propoxy isomers such as isopropoxy, n-propoxy, etc.), —$OC_4H_9$ (e.g. butyoxy isomers), —$OC_5H_{11}$ (e.g. pentoxy isomers), —$OC_6H_{13}$ (e.g. hexoxy isomers), —$OC_7H_{15}$ (e.g. heptoxy isomers), etc.

In aspects of this embodiment, a carvacrol compound is one of the following compounds:

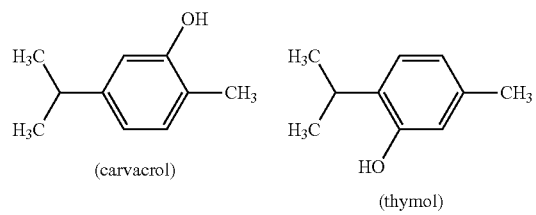

Aspects of the present specification disclose, in part a cumin compound and/or cumin compounds. Non-limiting examples of suitable cumin compounds include, e.g., cumin alcohol, cumin aldehyde and cuminic acid.

In an embodiment, a repellent compound is a cumin compound. In another embodiment, a repellent compound is a cumin compound having a structure of formula II:

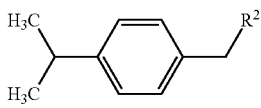

wherein $R^2$ is H, OH, =O, a halogen, a carbonyl group (CHO), a carboxyl group (OOH), or an optionally substituted alkyl, an alkoxy. In aspects of this embodiment, an optionally substituted alkyl is an optionally substituted $C_{1-6}$ alkyl. In other aspects of this embodiment, a halogen is F, Cl, Br, or I. In aspects of this embodiment, an alkoxy is —$OCH_3$, —$OC_2H_5$, —$OC_3H_7$, or —$OC_4H_9$.

In aspects of this embodiment, a cumin compound is one of the following compounds:

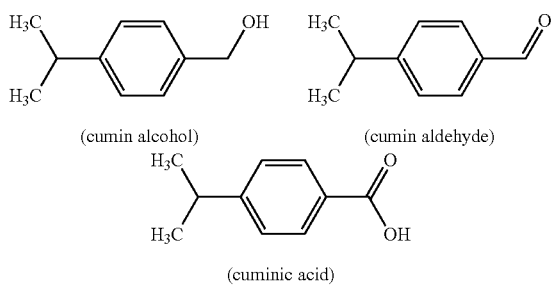

(cumin alcohol)      (cumin aldehyde)

(cuminic acid)

Aspects of the present specification disclose, in part a cinnamate compound and/or cinnamate compounds. Non-limiting examples of suitable cinnamate compounds include, e.g., cinnamate [(E)-3-phenylprop-2-enoate], methyl cinnamate (methyl 3-phenylprop-2-enoate), ethyl cinnamate (ethyl 3-phenylprop-2-enoate), butyl cinnamate (butyl 3-phenylprop-2-enoate), isobutyl-cinnamate (isobutyl 3-phenylprop-2-enoate), N-butyl-cinnamate (N-butyl 3-phenylprop-2-enoate), isopropyl-cinnamate (isopropyl 3-phenylprop-2-enoate), E-cinnamyl acetate, cinnamaldehyde [(2E)-3-phenylprop-2-enal], E-cinnamaldehyde, Z-cinnamaldehyde, and o-methoxycinnamaldehyde.

In an embodiment, a repellent compound is a cinnamate compound. In another embodiment, a repellent compound is a cinnamate compound having a structure of formula III:

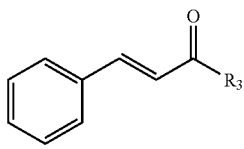

wherein $R^3$ is H, OH, =O, a halogen, or an optionally substituted alkyl, an alkoxy. In aspects of this embodiment, an optionally substituted alkyl is an optionally substituted $C_{1-6}$ alkyl. In other aspects of this embodiment, a halogen is F, Cl, Br, or I. In aspects of this embodiment, an alkoxy is —$OCH_3$, —$OC_2H_5$, —$OC_3H_7$, or —$OC_4H_9$.

In another embodiment, a repellent compound is a cinnamate compound having a structure of formula IV:

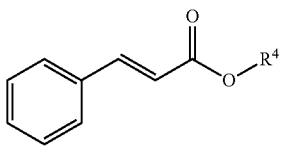

wherein $R^4$ is H, OH, =O, $CH_3$, a halogen, or an optionally substituted alkyl, an alkoxy. In aspects of this embodiment, an optionally substituted alkyl is an optionally substituted $C_{1-6}$ alkyl. In other aspects of this embodiment, a halogen is F, Cl, Br, or I. In aspects of this embodiment, an alkoxy is —$OCH_3$, —$OC_2H_5$, —$OC_3H_7$, or —$OC_4H_9$.

In a preferred embodiment, $R^4$ is a C1-C10 aliphatic substituent, preferably a C2-C10 aliphatic substituent. In a preferred embodiment, $R^4$ is a C1-C8 aliphatic substituent, preferably a C2-C8 aliphatic substituent. In a preferred embodiment, $R^4$ is a C1-C7 aliphatic substituent, preferably a C2-C7 aliphatic substituent, and most preferably, $R^4$ is a C1-C6 aliphatic substituent, preferably a C2-C6 aliphatic substituent. In an embodiment, $R^4$ is a C3-C10, preferably C3-C8, more preferably C3-C7 and most preferably C3-C6 aliphatic substituent.

For example, said aliphatic substituent is a substituted or unsubstituted alkyl or alkenyl.

Preferably, $R^4$ is a C1-C10, preferably C2-C10 alkyl. For example, $R^4$ is a C1-C7, preferably a C2-C7 alkyl. More preferably, $R^4$ is a C1-C10, preferably a C2-C6 alkyl.

In a preferred embodiment, $R^4$ is a C2-C10, preferably C3-C10 alkyl. For example, $R^4$ is a C2-C7, preferably a C3-C7 alkyl. More preferably, $R^4$ is a C2-C10, preferably a C3-C6 alkyl.

Cinnamate compounds having C2-C10, preferably C3-C10 aliphatic substituent were not found in essential oils but were surprisingly found to have high insect and arachnid repellency activity. Surprisingly, these cinnamate derivatives were found to have even higher insect and/or arachnid repellence activity than methyl cinnamate, the cinnamate compound that is naturally occurring in some essential oils. Therefore, the invention encompasses compositions comprising synthetic or natural compounds, for example compositions with different cinnamate compounds.

In aspects of this embodiment, a cinnamate compound is one of the following compounds:

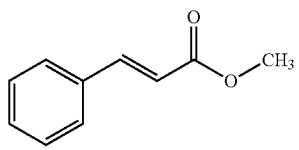

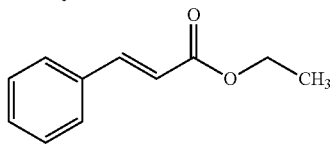

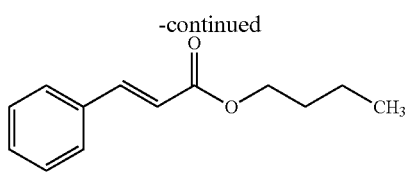

Aspects of the present specification provide, in part, a composition comprising a mosquito repellent disclosed herein. A composition disclosed herein comprises a repellent compound disclosed herein and is useful in repelling insects and/or arachnids, such as mosquitoes and ticks from an individual and/or a location treated with the composition. As such, a composition disclosed herein is useful for any application that reduces mosquito vector human host and/or animal host interactions. A composition may be administered to an individual alone, or in combination with other supplementary active ingredients, agents, or drugs.

A composition disclosed herein may comprise one or more repellent compounds disclosed herein. In one embodiment, a composition disclosed herein may comprise only a single repellent compound disclosed herein. In another embodiment, a composition disclosed herein may comprise a plurality of repellent compounds disclosed herein. In aspects of this embodiment, a composition disclosed herein comprises at least two repellent compounds, at least three repellent compounds, at least four repellent compounds, or at least five repellent compounds. In other aspects of this embodiment, a composition disclosed herein comprises at most two repellent compounds, at most three repellent compounds, or at most four repellent compounds. In yet other aspects of this embodiment, a composition disclosed herein comprises one to three repellent compounds, two to four repellent compounds, two to five repellent compounds, three to five repellent compounds, or two to three repellent compounds. In aspects of this embodiment, a repellent compound includes, without limitation, a carvacrol compound disclosed herein, a cinnamate compound disclosed herein, a cumin compound disclosed herein, or any combination thereof.

In an embodiment, the composition of the invention comprises a combination of two or more compounds having insect and/or arachnid repellent activity, said two or more compounds being selected, independently, from carvacrol compounds, cumin compounds, and cinnamate compounds.

In a preferred embodiment, the composition comprises at least one carvacrol compound. For example, the composition comprises carvacrol or thymol and one or more other insect repellent compounds disclosed herein. In an embodiment, the composition comprises carvacrol and thymol (two carvacrol compounds) and one or more other insect repellent compounds disclosed herein, for example one or more cumin compounds and/or one or more cinnamate compounds.

In an embodiment, the composition comprises carvacrol and one or more selected from the group consisting of thymol, a cumin compound and a cinnamate compound.

In an embodiment, the composition of the invention comprises at least a carvacrol compound and one or more selected from the group of a cumin compound and a cinnamate compound. Preferably, the composition comprises carvacrol and one or more selected from the group of a cumin compound and a cinnamate compound.

In an embodiment, the composition comprises carvacrol and one or more cumin compounds, for example one or more selected from cumin alcohol, cumin aldehyde and cuminic acid. In accordance with a preferred embodiment, the composition comprises carvacrol and one or more cumin compounds selected from cumin alcohol and cuminic acid.

Alternatively, the composition comprises thymol and one or more cumin compounds, for example one or more selected from cumin alcohol, cumin aldehyde and cuminic acid, preferably from cumin alcohol and cuminic acid.

In an embodiment, the composition comprises carvacrol and cumin alcohol. In a preferred embodiment, the composition comprises carvacrol and cuminic acid.

In an embodiment, the composition comprises carvacrol and one or more cinnamate compounds, for example carvacrol and one or more selected from methyl cinnamate and one or more cinnamate compounds of formula (IV) with $R^4$ being a C2-C10, preferably C3-C10 aliphatic substituent, for example a C2-C10 or C3-C10 alkyl, in accordance with the preferred embodiment specified herein above.

Alternatively, the composition comprises thymol and one or more selected from methyl cinnamate and one or more a cinnamate compound of formula (IV) with $R^4$ being a C2-C10, preferably C3-C10 aliphatic substituent, for example a C2-C10, preferably C3-C10 alkyl, in accordance with the preferred embodiment specified herein above.

In an embodiment, the composition comprises carvacrol and one or more C2-C10 alkyl cinnamate, preferably C2-C6 alkyl cinnamate, preferably ethyl- and/or butyl cinnamate.

In a preferred embodiment, the composition comprises carvacrol and one or more C3-C10 alkyl cinnamates, preferably a C3-C6 alkyl cinnamate, for example butyl-cinnamate.

In an embodiment, the composition comprises a carvacrol compound, a cumin compound and a cinnamate compound. For example, the composition comprises carvacrol, a cumin compound and a cinnamate compound. Alternatively, the composition comprises thymol, a cumin compound and a cinnamate compound.

In an embodiment, the composition comprises carvacrol, one or more cumin compounds selected from cumin alcohol, cumin aldehyde and cuminic acid, and one or more cinnamate compounds selected from methyl cinnamate and one or more cinnamate compounds of formula (IV) with $R^4$ being a C2-C10, preferably C3-C10 aliphatic substituent, for example a C2-C10 alkyl, preferably C2-C6 alkyl, more preferably a C3-C10 alkyl, such as a C3-C6 alkyl.

In a preferred embodiment, the composition comprises carvacrol, one or more cumin compounds selected from cumin alcohol, cumin aldehyde and cuminic acid, and one or more cinnamate compounds selected from compounds of formula (IV) with $R^4$ being a C2-C10, preferably C3-C10 aliphatic substituent, for example a C2-C10 or C3-C10 alkyl, preferably C2-C6 or C3-C6 alkyl, preferably from ethyl and butyl cinnamate.

In another embodiment, the composition comprises thymol, one or more cumin compounds selected from cumin alcohol, cumin aldehyde and cuminic acid, and one or more cinnamate compounds selected from methyl cinnamate and one or more cinnamate compounds of formula (IV) with $R^4$ being a C2-C10 aliphatic substituent, for example a C2-C10 alkyl, preferably C2-C6 alkyl. In an embodiment, R4 is a C3-C10 aliphatic substituent, for example a C3-C10 alkyl, preferably C3-C6 alkyl.

In an embodiment, the composition comprises carvacrol, one or more cumin compounds selected from cumin alcohol, cumin aldehyde and cuminic acid, and one or more cinnamate compounds selected from C2-C10 or C3-C10 alkyl, preferably C2-C6 or C3-C6 alkyl cinnamates.

In an embodiment, the composition comprises carvacrol, one or more cumin compounds selected from cumin alcohol, cumin aldehyde and cuminic acid, and one or more cinnamate compounds selected from ethyl and butyl cinnamate.

In a preferred embodiment, the composition comprises carvacrol, one selected from cuminic acid and cumin alcohol and one selected from ethyl cinnamate and butyl cinnamate.

In an embodiment, the composition comprises a cumin compound and a cinnamate compound. In an embodiment, the composition comprises one or more selected from the group consisting of cuminic acid, cumin alcohol and cumin aldehyde, and one or more selected from the group of methyl cinnamate, methyl cinnamate and one or more cinnamate compounds of formula (IV) with $R^4$ being a C2-C10 aliphatic substituent, for example a C2-C10 alkyl, preferably C2-C6 alkyl, preferably a C3-C10 aliphatic substituent, for example a C3-C10 alkyl, preferably C3-C6 alkyl.

In an embodiment, the composition comprises one or more selected from the group consisting of cuminic acid, cumin alcohol and cumin aldehyde, and one or more selected from cinnamate compounds of formula (IV) with $R^4$ being a C2-C10 aliphatic substituent, for example a C2-C10 alkyl, preferably C2-C6 alkyl. In an embodiment, R4 is a C3-C10 aliphatic substituent, for example a C3-C10 alkyl, preferably C3-C6 alkyl.

In an embodiment, the composition comprises one or more selected from the group consisting of cuminic acid, cumin alcohol and cumin aldehyde, and one or more selected from C2-C10, preferably C2-C6 alkyl cinnamates. Preferably, said cinnamate is a C3-C10, preferably a C3-C6 cinnamate.

In an embodiment, the composition comprises cumin aldehyde and one or more selected from C1-C10, preferably C2-C6 alkyl cinnamates. In an embodiment, the composition comprises cuminic acid and one or more selected from C1-C10, preferably C2-C6 alkyl cinnamates. In an embodiment, the composition comprises cumin alcohol and one or more selected from C1-C10, preferably C2-C6 alkyl cinnamates. Preferably, said alkyl is C3-C10, more preferably C3-C6 alkyl cinnamates.

In an embodiment, the composition of the invention comprises two different cumin compounds. Preferably, the composition comprises two or more selected from the group consisting of cuminic acid, cumin alcohol and cumin aldehyde. For example, the composition comprises cuminic acid and cumin aldehyde. In an embodiment, the composition comprises cuminic acid and cumin alcohol. In an embodiment, the composition comprises cumin aldehyde and cumin alcohol. In an embodiment, the composition comprises cuminic acid, cumin aldehyde and cumin alcohol.

In an embodiment, the composition comprises two or more cinnamate compounds. In an embodiment, the composition comprises methyl cinnamate, ethyl cinnamate and one or more cinnamate compounds of formula (IV) with $R^4$ being a C2-C10, in particular a C3-C10 aliphatic substituent, for example a C2-C10 alkyl, for example C3-C10 alkyl, preferably C2-C6 alkyl, more preferably C3-C6 alkyl. In an embodiment, the composition comprises two different cinnamate compounds selected from compounds of formula (IV) with $R^4$ being a C2-C10 aliphatic substituent, for example a C2-C10 alkyl, preferably C2-C6 alkyl.

In a preferred embodiment, the composition comprises two different cinnamate compounds selected from compounds of formula (IV) with $R^4$ being a C3-C10 aliphatic substituent, for example a C3-C10 alkyl, preferably C3-C6 alkyl.

In an embodiment, the composition of the invention comprises a carvacrol compound and a cinnamate compound. Preferably, the composition comprises carvacrol and one, two or more cinnamate compounds.

In an embodiment, the composition of the invention comprises a carvacrol compound and a cumin compound. Preferably, the composition comprises carvacrol and one, two or more cumin compounds.

In an embodiment, a composition disclosed herein includes a carvacrol compound. In aspects of this embodiment, a composition comprises, carvacrol, thymol, or any combination thereof.

In another embodiment, a composition disclosed herein includes a carvacrol compound and a cumin compound. In aspects of this embodiment, a composition comprises cumin alcohol, cumin aldehyde, cuminic acid, or any combination thereof.

In another embodiment, a composition disclosed herein includes a carvacrol compound and a cinnamate compound. In aspects of this embodiment, a composition comprises cinnamate, methyl cinnamate, ethyl cinnamate, butyl cinnamate, isobutyl-cinnamate, N-butyl cinnamate, isopropyl cinnamate, E-cinnamyl acetate, cinnamaldehyde, E-cinnamaldehyde, Z-cinnamaldehyde, o-methoxycinnamaldehyde, or any combination thereof.

In another embodiment, a composition disclosed herein comprises a carvacrol compound disclosed herein and a single additional repellent compound disclosed herein. In another embodiment, a composition disclosed herein comprises a carvacrol compound disclosed herein and one or more additional repellent compounds disclosed herein. In aspects of this embodiment, a composition disclosed herein comprises a carvacrol compound and at least one additional repellent compound, at least two additional repellent compounds, at least three additional repellent compounds, at least four additional repellent compounds. In other aspects of this embodiment, a composition disclosed herein comprises a carvacrol compound and at most one additional repellent compound, at most two additional repellent compounds, at most three additional repellent compounds, at most four additional repellent compounds. In yet other aspects of this embodiment, a pharmaceutical composition disclosed herein comprises a carvacrol compound and one to three additional repellent compounds, two to four additional repellent compound, two to three additional repellent compounds, two to five additional repellent compound, or three to five additional repellent compound. In aspects of this embodiment, an additional repellent compound includes, without limitation, a cinnamate compound disclosed herein, a cumin compound disclosed herein, or any combination thereof.

In another embodiment, a composition disclosed herein comprises a cinnamate compound disclosed herein and a single additional repellent compound disclosed herein. In another embodiment, a composition disclosed herein comprises a cinnamate compound disclosed herein and one or more additional repellent compounds disclosed herein. In aspects of this embodiment, a composition disclosed herein comprises a cinnamate compound and at least one additional repellent compound, at least two additional repellent compounds, at least three additional repellent compounds, at least four additional repellent compounds. In other aspects of this embodiment, a composition disclosed herein comprises a cinnamate compound and at most one additional repellent compound, at most two additional repellent compounds, at most three additional repellent compounds, at most four additional repellent compounds. In yet other aspects of this embodiment, a pharmaceutical composition disclosed herein comprises a cinnamate compound and one to three additional repellent compounds, two to four additional repellent compound, two to three additional repellent compounds, two to five additional repellent compound, or three to five additional repellent compound. In aspects of this embodiment, an additional repellent compound includes, without limitation, a carvacrol compound disclosed herein, a cumin compound disclosed herein, or any combination thereof.

In another embodiment, a composition disclosed herein comprises a cumin compound disclosed herein and a single additional repellent compound disclosed herein. In another embodiment, a composition disclosed herein comprises a cumin compound disclosed herein and one or more additional repellent compounds disclosed herein. In aspects of this embodiment, a composition disclosed herein comprises a cumin compound and at least one additional repellent compound, at least two additional repellent compounds, at least three additional repellent compounds, at least four additional repellent compounds. In other aspects of this embodiment, a composition disclosed herein comprises a cumin compound and at most one additional repellent compound, at most two additional repellent compounds, at most three additional repellent compounds, at most four additional repellent compounds. In yet other aspects of this embodiment, a pharmaceutical composition disclosed herein comprises a cumin compound and one to three additional repellent compounds, two to four additional repellent compound, two to three additional repellent compounds, two to five additional repellent compound, or three to five additional repellent compound. In aspects of this embodiment, an additional repellent compound includes, without limitation, a carvacrol compound disclosed herein, a cinnamate compound disclosed herein, or any combination thereof.

In another embodiment, a composition disclosed herein includes a carvacrol compound disclosed herein, a cinnamate compound disclosed herein, and a cumin compound disclosed herein.

In another embodiment, a composition disclosed herein comprises a cinnamate compound and one or more additional repellent compounds disclosed herein, wherein the one or more additional repellent compounds does not include a carvacrol compound disclosed herein. In an aspect of this embodiment, a composition disclosed herein comprises a cinnamate compound and one or more additional repellent compounds, wherein the one or more additional repellent compounds does not include a cumin compound.

In another embodiment, a composition disclosed herein comprises a cumin compound and one or more additional repellent compounds disclosed herein, wherein the one or more additional repellent compounds does not include a carvacrol compound disclosed herein. In an aspect of this embodiment, a composition disclosed herein comprises a cumin compound and one or more additional repellent compounds, wherein the one or more additional repellent compounds does not include a cinnamate compound.

In another embodiment, a composition disclosed herein comprises a carvacrol compound and one or more additional repellent compounds disclosed herein, wherein the one or more additional repellent compounds does not include a cinnamate compound disclosed herein. In an aspect of this embodiment, a composition disclosed herein comprises a carvacrol compound and one or more additional repellent compounds, wherein the one or more additional repellent compounds does not include a cumin compound.

In another embodiment, a composition disclosed herein comprises a cinnamate compound and a cumin compound and one or more additional repellent compounds disclosed herein, wherein the one or more additional repellent compounds do not include a carvacrol compound disclosed herein. In an aspect of this embodiment, a composition disclosed herein comprises a cumin compound and one or more additional repellent compounds, wherein the one or more additional repellent does neither include a carvacrol compound nor a cinnamate compound For making the composition in the invention, it is possible to add, independently, one, two or more compounds having insect and/or arachnid repellent activity as isolated and/or synthetic compounds to said composition. It is also possible to add one or more compounds in the form of one or more essential oils, fraction or concentrate thereof, wherein said compound is comprised in said essential oil, fraction or concentrate.

Practically, most compounds of the compositions of the invention are readily available in the form of essential oils comprising the compounds or as isolates from such essential oils. Cinnamate compounds of formula (IV) with $R^4$ being a C3-C10 aliphatic substituent may not all so far be known from essential oils and may thus preferably be prepared by at least one chemical synthesis step, for example using cinnamate obtained from essential oils. Of course, also compounds that can be isolated from essential oils may be obtained by synthesis. Furthermore, preparation of compounds my biotechnological means and/or by an overall process including one or more steps including isolation from an essential oil, biotechnological conversion and/or synthesis can be employed. The present invention is not intended to be limited to any particular way of obtaining the compounds disclosed in this specification.

The composition of the invention may be based on compounds or fractions of extracts isolated from plant that are combined in accordance with the invention. In a preferred embodiment, the composition of the invention comprises or consists of a combination of two or more essential oils or essential oil fractions.

In an embodiment, the composition of the invention comprises one or more selected from the groupings: (i) a combination of two (or more) different essential oils, (ii) a combination of an essential oil with a fraction of a different essential oil, (iii) a combination of two fractions from two different essential oils, and (iv) two different fractions of the same essential oil.

In an aspect, the invention provides a composition comprising a combination of two or more different essential oils and fractions thereof, wherein said essential oils are selected from the group consisting of: essential oil (EO) of (1) the aerial plat parts of *Coridothymus capitatus* (EO 5), (2) aerial plat parts of *Origanum majorana* (EO 6), (3) leaves of *Origanum heracleoticum* (EO 9), (4) flowers of *Origanum vulgare* (EO 14) and (5) leaves of *Origanum* sp. (EO 169).

In an embodiment, the composition of the invention is an insect and/or arachnid repellent composition. Preferably, the composition has an insect and/or arachnid repellence activity. In an embodiment, a composition disclosed herein reduces insect and/or arachnid mammalian host interactions In an embodiment, a composition disclosed herein reduces the ability of an insect and/or arachnid to obtain a blood-meal from a mammal. Preferably, said insect and/or arachnid is selected from a blood-feeding insect and/or arachnid, for example selected from mosquitos, sand flies and ticks.

The composition of the invention can be used to repel insects from humans and animals, and reduces arthropod-host interactions in general, not only with respect to humans.

An individual, for the purpose of this specification, may be a human or animal individual, for example a livestock or companion animal individual. Mammals, for the purpose of this specification, include humans and/or animals, in particular humans and mammalian animals, such as mammalian pets and livestock animals, for example. Animals include also non-mammalian animals, in particular non-mammalian livestock animals and/or pets, such as birds, poultry, and so forth.

In aspects of this embodiment, presence of a composition (1) repels insect and/or arachnid (2) reduces insect and/or arachnid mammalian host interactions and/or (3) reduces the ability of an insect and/or arachnid to obtain a blood-meal from a mammal by, e.g., at least 10%, at least 15%, at least 20%, at least 30%, at least 40%, at least 50%, at least 60%, at least 70%, at least 80%, or at least 90%, as compared to not having the composition present. In other aspects of this embodiment, presence of a composition (1) repels insects and/or arachnids; (2) reduces insect and/or arachnid mammalian host interactions; and/or (3) reduces an ability of an insect and/or arachnid to obtain a blood-meal from a mammal by, e.g., about 10% to about 100%, about 30% to about 100%, about 50% to about 100%, about 70% to about 100%, about 20% to about 90%, about 40% to about 90%, about 60% to about 90%, about 10% to about 80%, about 30% to about 80%, about 50% to about 80%, about 10% to about 70%, about 30% to about 70%, or about 50% to about 70%, as compared to not having the composition present.

A composition disclosed herein can take any of a variety of dosage forms including, without limitation, a liquid composition, such as, e.g., a solution, suspension, emulsion; a semi-solid composition, such as, e.g., an ointment, cream, balm, foam, gel, or salve or a solid composition, such as, e.g., lyophilisate, powder, granule, pellet, capsule; or any other dosage form suitable for applying a repellent compound/composition disclosed herein to a location to be treated. In one embodiment, in liquid, semi-solid, and solid forms, an amount of a repellent compound disclosed herein typically is between about 0.0001% (w/v) to about 50% (w/v), about 0.001% (w/v) to about 10.0% (w/v), or about 0.01% (w/v) to about 1.0% (w/v). In another aspect embodiment, in liquid, semi-solid, and solid forms, an amount of a repellent compound disclosed herein typically is applied between about 0.001 $\mu g/cm^2$ to about 500 $\mu g/cm^2$, about 0.01 $\mu g/cm^2$ to about 100 $\mu g/cm^2$, or about 0.1 $\mu g/cm^2$ to about 10 $\mu g/cm^2$. In another aspect embodiment, in liquid, semi-solid, and solid forms, an amount of a repellent compound disclosed herein typically is between about 0.01 $nmole/cm^2$ to about 1000 $nmole/cm^2$, about 0.1 $nmole/cm^2$ to about 100 $nmole/cm^2$, or about 1 $nmole/cm^2$ to about 50 $nmole/cm^2$. In another embodiment, in liquid, semi-solid, and solid forms, an amount of a repellent compound disclosed herein is typically between about 0.001 mg/L to about 500 mg/L, about 0.01 mg/L to about 100 mg/L, or about 0.1 mg/L to about 50 mg/L.

It is noted in general terms that the skilled person will understand that the concentration of the insect repellent compounds in the composition of the invention will be adjusted in accordance with the type of formulation (slow, fast release, excipients), the physical location such as on skin, animal fur, clothing or in a room, the temperature and/or humidity conditions of the location, and the product type. The composition of the invention may in particular be used in diverse products, including, for example, topically administered products, compositions for use in connection with an evaporation device such dispensing from a wick, sprays, just to mention a few, as disclosed elsewhere in this specification.

In another embodiment, a composition disclosed herein comprises, when applied, about 0.01 $\mu g/cm^2$ to about 50 $\mu g/cm^2$ of a carvacrol compound disclosed herein, about 0.01 $\mu g/cm^2$ to about 50 $\mu g/cm^2$ of a cumin compound disclosed herein, and/or about 0.01 $\mu g/cm^2$ to about 50 $\mu g/cm^2$ of a cinnamate compound disclosed herein. In aspects of this embodiment, a composition disclosed herein comprises when applied, about 0.1 $\mu g/cm^2$ to about 10 $\mu g/cm^2$ of a carvacrol compound disclosed herein, about 0.1 $\mu g/cm^2$ to about 10 $\mu g/cm^2$ of a cumin compound disclosed herein, and/or about 0.1 $\mu g/cm^2$ to about 10 $\mu g/cm^2$ of a cinnamate compound disclosed herein. In aspects of this embodiment, a composition disclosed herein comprises, when applied, about 0.5 $\mu g/cm^2$ to about 5 $\mu g/cm^2$ of a carvacrol compound disclosed herein, about 0.5 $\mu g/cm^2$ to about 5 $\mu g/cm^2$ of a cumin compound disclosed herein, and/or about 0.5 $\mu g/cm^2$ to about 5 $\mu g/cm^2$ of a cinnamate compound disclosed herein.

In another embodiment, a composition disclosed herein comprises, when applied, about 0.01 $nmole/cm^2$ to about 100 $nmole/cm^2$ of a carvacrol compound disclosed herein, about 0.01 $nmole/cm^2$ to about 100 $nmole/cm^2$ of a cumin compound disclosed herein, and/or about 0.01 $nmole/cm^2$ to about 100 $nmole/cm^2$ of a cinnamate compound disclosed herein. In aspects of this embodiment, a composition disclosed herein comprises, when applied, about 0.1 $nmole/cm^2$ to about 50 $nmole/cm^2$ of a carvacrol compound disclosed herein, about 0.1 $nmole/cm^2$ to about 50 $nmole/cm^2$ of a cumin compound disclosed herein, and/or about 0.1 $nmole/cm^2$ to about 50 $nmole/cm^2$ of a cinnamate compound disclosed herein. In aspects of this embodiment, a composition disclosed herein comprises, when applied, about 1 $nmole/cm^2$ to about 30 $nmole/cm^2$ of a carvacrol compound disclosed herein, about 1 $nmole/cm^2$ to about 30 $nmole/cm^2$ of a cumin compound disclosed herein, and/or about 1 $nmole/cm^2$ to about 30 $nmole/cm^2$ of a cinnamate compound disclosed herein. In aspects of this embodiment, a composition disclosed herein comprises, when applied, about 2.5 $nmole/cm^2$ to about 25 $nmole/cm^2$ of a carvacrol compound disclosed herein, about 2.5 $nmole/cm^2$ to about 25 $nmole/cm^2$ of a cumin compound disclosed herein, and/or about 2.5 $nmole/cm^2$ to about 25 $nmole/cm^2$ of a cinnamate compound disclosed herein.

A composition disclosed herein may optionally comprise additional components such as, e.g., an adhesive, a solvent, a wetting agent, an emulsifying agent, a carrier, a diluent, or a dispersing agent. Such additional components are known to a person of skill in the art.

A composition disclosed herein may optionally comprise an additional mosquito repellent. Non-limiting examples of an additional mosquito repellent, include, e.g., DEET, ethyl-butylacetylaminopropionate (EBAAP), and Picaridine.

A composition disclosed herein may optionally comprise an insecticide. Non-limiting examples of an insecticide include a organochlorine, such as, e.g., Aldrin, Chlordane, Chlordecone, DDT, Dieldrin, Endosulfan, Endrin, Heptachlor, Hexachlorobenzene, Lindane (gamma-hexachlorocyclohexane), Methoxychlor, Mirex, Pentachlorophenol, and TDE; an organophosphate, such as, e.g., Acephate, Azinphos-methyl, Bensulide, Chlorethoxyfos, Chlorpyrifos, Chlorpyriphos-methyl, Diazinon, Dichlorvos (DDVP), Dicrotophos, Dimethoate, Disulfoton, Ethoprop, Fenamiphos, Fenitrothion, Fenthion, Fosthiazate, Malathion, Methamidophos, Methidathion, Mevinphos, Monocrotophos, Naled, Omethoate, Oxydemeton-methyl, Parathion, Parathion-methyl, Phorate, Phosalone, Phosmet, Phostebupirim, Phoxim, Pirimiphos-methyl, Profenofos, Terbufos, Tetrachlorvinphos, Tribufos, and Trichlorfon; a carbamate, such as, e.g., Aldicarb, Bendiocarb, Carbofuran, Carbaryl, Dioxacarb, Fenobucarb, Fenoxycarb, lsoprocarb, Methomyl, and 2-(1-Methylpropyl)phenyl methylcarbamate; a pyrethroid, such as, e.g., Allethrin, Bifenthrin, Cyhalothrin, A-Cyhalothrin, Cypermethrin, Cyfluthrin, Deltamethrin, Etofenprox, Fenvalerate, Permethrin, Phenothrin, Prallethrin, Resmethrin, Tetramethrin, Tralomethrin, and Transfluthrin; and a neonicotinoid, such as, e.g., Acetamiprid, Clothianidin, Imidacloprid, Nitenpyram, Nithiazine, Thiacloprid, and Thiamethoxam.

Aspects of the present specification disclose a method of reducing or preventing bites by mosquitoes and other blood-sucking arthropods on an individual animal or human by applying a repellent compound or composition disclosed herein to the individual, wherein such application of the repellent compound or composition repels a mosquito or other arthropod from the individual, thereby reducing or preventing bites for a blood-meal. In one embodiment, a repellent compound or composition disclosed herein is applied to an individual in order to repel a mosquito or other blood-sucking arthropod from obtaining a blood-meal from the individual treated. An individual may be any mammal. In an aspect of this embodiment, a mammal is a human being. Application of the compound or composition may be administered topically using, e.g., a lotion, an oil, an ointment, a cream, a balm, a foam, a gel, or salve.

Aspects of the present specification disclose a method of reducing or preventing a mosquito infestation to a location by applying a repellent compound or composition disclosed herein to the location, wherein such application repels mosquitoes or other blood-sucking arthropods from the location, thereby reducing or preventing the mosquito infestation. In another embodiment, the disclosed method is a method of treating a natural area by applying a repellent compound or composition disclosed herein, wherein such application repels a mosquito or other blood-sucking arthropod from foraging for a blood-meal in the vicinity of the treated natural area. Non-limiting examples of a natural area, include, e.g., a park area, a forested area, an area containing foliage, a pond area or any other area containing standing water. In another embodiment, the disclosed method is a method of treating a man-made structure by applying a repellent compound disclosed herein, wherein such application repels a mosquito from foraging for a blood-meal in the vicinity of the treated structure. Non-limiting examples of a man-made structure include, e.g., a building or part thereof such as a room, a balcony or terrace, a pool, a recreational area, a maintenance space for domestic animals, for example an incubator-maintenance space for birds including chicken.

As used herein, the term "location" refers to any site to which movement of a mosquito or other blood-sucking arthropod is to be retarded. A location includes, by way of example, a plant or group of plants, a particular area of land, or a man-made structure, such as, e.g., a commercial building, a house, a shed, other physical structure, or part thereof. As used herein, the term "plant" refers to any living organism belonging to the Kingdom Plantae. Non-limiting examples include trees, flowering plant, herbs, bushes, grasses, vines, ferns, mosses, and green algae.

A repellent compound or composition disclosed herein is applied to a location by any method that can dispense to a location an amount of repellent compound effective in repelling a mosquito or other blood-sucking arthropod. A method of application is not critical and many well known methods can be used.

In one embodiment, an appropriate amount of a repellent compound or composition disclosed herein can be dissolved into an appropriate compatible solvent and dispensed as a solution into or onto the intended location. The solvent employed is typically a volatile solvent (i.e., having a boiling point of about 100° C. or less) that will evaporate over a period of time.

In another embodiment, an appropriate amount of a repellent compound or composition disclosed herein can be combined with an appropriate propellant and used as a spray for application into or onto the intended location.

In another embodiment, a repellent compound or composition disclosed herein can be impregnated into a compatible matrix. As used herein, the term "compatible matrix" refers to any material in which one or more repellent compounds or compositions disclosed herein are either soluble, miscible, or penetrate into and where the material does not significantly alter or degrade a repellent activity of the one or more repellent compounds/compositions. In aspects of this embodiment, a compatible matrix does not significantly alter or degrade a repellent activity of one or more repellent compounds/compositions over a period of, e.g., at least 7 days, at least 14 days, at least 21 days, at least 28 days, at least 35 days, at least 42 days, at least 49 days, at least 56 days, or at least 63 days. Impregnation of a repellent compound/composition into the compatible matrix can be achieved by any well known methods known in the art. For example, a repellent compound or composition disclosed herein may be dissolved into a compatible volatile solvent and the resulting solution added to the matrix whereupon evaporation of the solvent results in impregnation of the repellent compound into the compatible matrix. In this regard, the matrix can be cotton twine, polymers such as, e.g., polyvinyls, polyisoprenes, polyethylene, polypropylene or copolymers thereof, or polybutenes. In another example, heating thins a compatible matrix and then a repellent compound/composition is added directly thereto. The mixture can then be combined with twine or other compatible matrices. A compatible matrix disclosed herein may be employed by itself or incorporated into a device used to house the matrix.

In another embodiment, a repellent compound or composition disclosed herein can be incorporated into a controlled-release device which dispenses the repellent compound or composition over time in a regulated or predictable manner. A controlled-release device disclosed herein may be employed by itself or incorporated into another device used to house the controlled-release device.

One type of controlled-release device is a "reservoir" device where the repellent compound or composition disclosed herein forms a core surrounded by an inert diffusion barrier. An inert diffusion barrier includes membranes that are non-porous, homogeneous polymeric films, through which transport occurs by a process of dissolution of the permeating species in the polymer at one interface and diffusion down a gradient in thermodynamic activity. These membranes are usually referred to as solution-diffusion membranes. Another class of inert diffusion barrier includes the porous and/or fibrous barriers such as, for example, hollow fibers, porous and/or fibrous materials, in which a repellent compound or composition diffuses mainly by capillary forces or is introduced into the material by impregnation. Other less common reservoir devices are designed to enable diffusion to take place by mechanical pumping or under external forces, such as, e.g., gravity, electrical field, vacuum, or centrifugal forces. A reservoir device can exist in a variety of shapes, and can be degradable or non-degradable.

In an aspect of this embodiment, a reservoir device is a microcapsule comprising a core of a repellent compound or composition disclosed herein surrounded by a coating or shell of, e.g., a polyvinyl chloride (PVC) polyvinyl acetate (PVA) plastic. Size typically varies from about 1 µm to about 1000 µm and can have irregular or geometric shapes. Core payload usually varies from 0.1 to 98 weight percent. Encapsulation processes are often loosely classified as either chemical or mechanical. Examples of chemical processes include but are not limited to complex coacervation, polymer-polymer incompatibility, interfacial polymerization in liquid media, in situ polymerization, in-liquid drying, thermal and ionic gelation in liquid media, desolvation in liquid media, starch-based chemistry processes, trapping in cyclodextrins, and formation of liposomes. Examples of mechanical processes include but are not limited to spray drying, spray chilling, fluidized bed, electrostatic deposition, centrifugal extrusion, spinning disk or rotational suspension separation, annular-jet encapsulation, polymerization at liquid-gas or solid-gas interface, solvent evaporation, pressure extrusion or spraying into solvent extraction bath.

Another type of controlled-release device is a "monolithic" device where a repellent compound or composition disclosed herein is dissolved or dispersed throughout a substantially inert matrix from which the repellent compound or composition disclosed herein is gradually released. Non-limiting examples of matrices included in a monolithic device include various gels, waxes, gelatins, natural resins, rubbers, elastomers, synthetic and natural polymers. A monolithic device can exist in a variety of shapes, and can be degradable or non-degradable. Size can vary depending on the application. For example, a monolithic device can be produced as a microcapsule having a size of about 1 µm to about 1000 µm with irregular or geometric shapes. As another example, a monolithic device can have a size of about 1 mm to about 10 cm with irregular or geometric shape.

A controlled-release device disclosed herein can be a liquid composition or a solid composition. A liquid sustained-release formulation includes a repellent compound or composition disclosed herein, a solvent, and typically further comprise of surface active agents to render the composition readily dispersible in water, such agents include a wetting agent, an emulsifying agent, or a dispersing agent. In one embodiment, a liquid form of a sustained-release formulation is an emulsion formulation, such as, e.g., a water in oil (w/o) emulsion or oil in water (o/w) emulsion. Non-limiting examples of oils include vegetable oils and mineral oils. Droplet size can vary from the nanometer scale (colloidal dispersion) to several hundred microns. A variety of surfactants and thickeners are usually incorporated in the formulation to modify the size of the droplets, stabilize the emulsion, and modify the release.

A solid form of controlled-release device comprises a solid substrate like porous particulates such as silica, perlite, talc, clay, pyrophyllite, diatomaceous earth, gelatin and gels, polymers (e.g., polyurea, polyurethane, polyamide, polyester, etc.), polymeric particles, or cellulose. These include, for example, hollow fibers, hollow tubes or tubing which release a repellent compound or composition disclosed herein through the walls, capillary tubing which releases the compound or composition out of an opening in the tubing, polymeric blocks of different shapes, e.g., strips, blocks, tablets, discs, which release the compound out of the polymer matrix, membrane systems which hold the repellent compound within an impermeable container and release it through a measured permeable membrane, and combinations of the foregoing. Examples of other dispensing means are polymer laminates, polyvinyl chloride pellets, and microcapillaries.

Controlled release can also be achieved by a number of other methods such as, e.g., complexation of a repellent compound or composition disclosed herein, slowly dissolving coatings, erosion, microbial action, or use of derivatives or new compounds of reduced solubility or volatility.

In aspects of this embodiment, a controlled-release device releases a repellent compound or composition disclosed herein with substantially zero order release kinetics over a period of, e.g., about 1 day, about 3 days, about 7 days, about 15 days, about 30 days, about 45 days, about 60 days, about 75 days, or about 90 days. In other aspects of this embodiment, a controlled-release device releases a repellent compound or composition disclosed herein with substantially zero order release kinetics over a period of, e.g., at least 1 day, at least 3 days, at least 7 days, at least 15 days, at least 30 days, at least 45 days, at least 60 days, at least 75 days, or at least 90 days. In other aspects of this embodiment, a controlled-release device releases a repellent compound or composition disclosed herein with substantially zero order release kinetics over a period of between, e.g., about 1 day to about 7 days, about 1 day to about 15 days, about 1 day to about 30 days, about 7 days to about 30 days, about 15 days to about 45 days, about 30 days to about 60 days, about 45 days to about 75 days, or about 60 days to about 90 days.

In aspects of this embodiment, a controlled-release device releases a repellent compound or composition disclosed herein with substantially first order release kinetics over a period of, e.g., about 1 day, about 3 days, about 7 days, about 15 days, about 30 days, about 45 days, about 60 days, about 75 days, or about 90 days. In other aspects of this embodiment, a controlled-release device releases a repellent compound or composition disclosed herein with substantially first order release kinetics over a period of, e.g., at least 1 day, at least 3 days, at least 7 days, at least 15 days, at least 30 days, at least 45 days, at least 60 days, at least 75 days, or at least 90 days. In other aspects of this embodiment, a controlled-release device releases a repellent compound or composition disclosed herein with substantially first order release kinetics over a period of between, e.g., about 1 day to about 7 days, about 1 day to about 15 days, about 1 day to about 30 days, about 7 days to about 30 days, about 15 days to about 45 days, about 30 days to about 60 days, about 45 days to about 75 days, or about 60 days to about 90 days.

Regardless of the method of application, the amount of a repellent compound or composition disclosed herein is a repellent effective amount, i.e., it is an amount sufficient to retard the movement of mosquitoes or other blood-feeding arthropod to the selected individual or location. In aspects of this embodiment, a repellent compound or composition disclosed herein is applied at a rate of, e.g., about 0.01 mg/m$^2$, about 0.025 mg/m$^2$, about 0.05 mg/m$^2$, about 0.075 mg/m$^2$, about 0.1 mg/m$^2$, about 0.25 mg/m$^2$, about 0.5 mg/m$^2$, about 0.75 mg/m$^2$, about 1 mg/m$^2$, about 2.5 mg/m$^2$, about 5 mg/m$^2$, about 7.5 mg/m$^2$, about 10 mg/m$^2$, or about 50 mg/m$^2$. In other aspects of this embodiment, a repellent compound or composition disclosed herein is applied at a rate of, e.g., at least 0.01 mg/m$^2$, at least 0.025 mg/m$^2$, at least 0.05 mg/m$^2$, at least 0.075 mg/m$^2$, at least 0.1 mg/m$^2$, at least 0.25 mg/m$^2$, at least 0.5 mg/m$^2$, at least 0.75 mg/m$^2$, at least 1 mg/m$^2$, at least 2.5 mg/m$^2$, at least 5 mg/m$^2$, at least 7.5 mg/m², at least 10 mg/m², or at least 50 mg/m². In yet other aspects of this embodiment, a repellent compound or composition disclosed herein is applied at a rate of, between e.g., about 0.01 mg/m² to about 50 mg/m², about 0.01 mg/m² to about 10 mg/m², about 0.01 mg/m² to about 1 mg/m², about 0.01 mg/m² to about 0.1 mg/m², about 0.05 mg/m² to about 50 mg/m², about 0.05 mg/m² to about 10 mg/m², about 0.05 mg/m² to about 1 mg/m², about 0.05 mg/m² to about 0.1 mg/m², about 0.05 mg/m² to about 5 mg/m², or about 0.05 mg/m² to about 0.5 mg/m².

Aspects of the present specification may also be described as follows:

1. A composition comprising a plurality of repellent compounds from diverse sources having mosquito repellent activity.

2. A composition comprising a combination of two or more compounds having insect and/or arachnid repellent activity, with the said two or more compounds being selected, independently, from carvacrol compounds, cumin compounds, and cinnamate compounds.

3. The composition according to embodiment 1 or 2, wherein the plurality of repellent compounds includes a carvacrol compound, a cumin compound, a cinnamate compound, or any combination thereof.

4. A composition comprising a carvacrol compound and one or more additional repellent compounds having mosquito and blood-sucking arthropod repellent activity.

5. The composition according to any one of the preceding embodiments, wherein one or more additional repellent compounds includes a cumin compound, a cinnamate compound, or any combination thereof.

6. A composition comprising a carvacrol compound and a cumin compound, wherein the composition has mosquito repellent activity.

7. A composition comprising a carvacrol compound and a cinnamate compound, wherein the composition has mosquito and blood-sucking arthropod repellent activity.

8. A composition comprising a carvacrol compound, a cumin compound, and a cinnamate compound, herein the composition has mosquito and blood-sucking arthropod repellent activity.

9. The composition according to embodiments 1-8, wherein the composition has mosquito and blood-sucking arthropod repellent activity.

10. The composition according to embodiment 9, wherein presence of the composition repels mosquitoes and blood-sucking arthropods by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, as compared to not having the composition present.

11. The composition according to embodiments 1-10, wherein the composition reduces an interaction between a blood-feeding arthropod and a mammal, in particular a mosquito-mammalian host interaction.

12. The composition according to embodiment 11, wherein the composition reduces said interaction by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

13. The composition according to embodiments 1-12, wherein the composition reduces an ability of a blood-feeding arthropod, in particular a mosquito, to obtain a blood-meal from a mammal.

14. The composition according to embodiment 13, wherein the composition reduces said ability by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

15. The composition according to embodiments 1-14, wherein the applied composition comprises about 0.01 µg/cm² to about 50 µg/cm² of a carvacrol compound, about 0.1 µg/cm² to about 10 µg/cm² of a carvacrol compound, or about 0.5 µg/cm² to about 5 µg/cm² of a carvacrol compound.

16. The composition according to embodiments 1-15, wherein the applied composition comprises about 0.01 µg/cm² to about 50 µg/cm² of a cumin compound, about 0.1 µg/cm² to about 10 µg/cm² of a cumin compound, or about 0.5 µg/cm² to about 5 µg/cm² of a cumin compound.

17. The composition according to embodiments 1-16, wherein the applied composition comprises about 0.01 µg/cm² to about 50 µg/cm² of a cinnamate compound, about 0.1 µg/cm² to about 10 µg/cm² of a cinnamate compound, or about 0.5 µg/cm² to about 5 µg/cm² of a cinnamate compound.

18. The composition according to embodiments 1-17, wherein the applied composition comprises about 0.01 nmole/cm² to about 200 nmole/cm² of a carvacrol compound, about 0.1 nmole/cm² to about 50 nmole/cm² of a carvacrol compound, about 1 nmole/cm² to about 30 nmole/cm² of a carvacrol compound, or about 2.5 nmole/cm² to about 25 nmole/cm² of a carvacrol compound.

19. The composition according to embodiments 1-18, wherein the applied composition comprises about 0.01 nmole/cm² to about 200 nmole/cm² of a cumin compound, about 0.1 nmole/cm² to about 50 nmole/cm² of a cumin compound, about 1 nmole/cm² to about 30 nmole/cm² of a cumin compound, or about 2.5 nmole/cm² to about 25 nmole/cm² of a cumin compound.

20. The composition according to embodiments 1-19 wherein the applied composition comprises about 0.01 nmole/cm² to about 200 nmole/cm² of a cinnamate compound, about 0.1 nmole/cm² to about 50 nmole/cm² of a cinnamate compound, about 1 nmole/cm² to about 30 nmole/cm² of a cinnamate compound, or about 2.5 nmole/cm² to about 25 nmole/cm² of a cinnamate compound.

21. The composition according to embodiments 1-20, wherein the applied composition comprises about 0.01 µg/cm² to about 50 µg/cm² of a carvacrol compound, about 0.01 µg/cm² to about 50 µg/cm² of a cumin compound disclosed herein, and about 0.01 µg/cm² to about 50 µg/cm² of a cinnamate compound.

22. The composition according to embodiments 1-21, wherein the applied composition comprises about 0.1 µg/cm² to about 10 µg/cm² of a carvacrol compound, about 0.1 µg/cm² to about 10 µg/cm² of a cumin compound, and about 0.1 µg/cm² to about 10 µg/cm² of a cinnamate compound.

23. The composition according to embodiments 1-22, wherein the applied composition comprises about 0.5 µg/cm² to about 5 µg/cm² of a carvacrol compound, about 0.5 µg/cm² to about 5 µg/cm² of a cumin compound, and about 0.5 µg/cm² to about 5 µg/cm² of a cinnamate compound.

24. The composition according to embodiments 1-23, wherein the applied composition comprises about 0.01 nmole/cm² to about 100 nmole/cm² of a carvacrol compound, about 0.01 nmole/cm² to about 200 nmole/cm² of a cumin compound, and about 0.01 nmole/cm$^2$ to about 200 nmole/cm$^2$ of a cinnamate compound.

25. The composition according to embodiments 1-24, wherein the applied composition comprises about 0.1 nmole/cm$^2$ to about 50 nmole/cm$^2$ of a carvacrol compound, about 0.1 nmole/cm$^2$ to about 50 nmole/cm$^2$ of a cumin compound, and about 0.1 nmole/cm$^2$ to about 50 nmole/cm$^2$ of a cinnamate compound.

26. The composition according to embodiments 1-25, wherein the applied composition comprises about 1 nmole/cm$^2$ to about 30 nmole/cm$^2$ of a carvacrol compound, about 1 nmole/cm$^2$ to about 30 nmole/cm$^2$ of a cumin compound, and about 1 nmole/cm$^2$ to about 30 nmole/cm$^2$ of a cinnamate compound.

27. The composition according to embodiments 1-26, wherein the applied composition comprises about 2.5 nmole/cm$^2$ to about 25 nmole/cm$^2$ of a carvacrol compound, about 2.5 nmole/cm$^2$ to about 25 nmole/cm$^2$ of a cumin compound, and about 2.5 nmole/cm$^2$ to about 25 nmole/cm$^2$ of a cinnamate compound.

28. The composition according to embodiments 1-28, wherein the carvacrol compound includes carvacrol, thymol, or any combination thereof.

29. The composition according to embodiments 1-28, wherein the cumin compound includes cumin alcohol, cumin aldehyde, cuminic acid, or any combination thereof.

30. The composition according to embodiments 1-29, wherein the cinnamate compound includes cinnamate, methyl cinnamate, ethyl cinnamate, butyl cinnamate, isobutyl-cinnamate, N-butyl-cinnamate, isopropyl-cinnamate, E-cinnamyl acetate, cinnamaldehyde, E-cinnamaldehyde, Z-cinnamaldehyde, o-methoxycinnamaldehyde, or any combination thereof.

31. A method of reducing bites by blood-feeding arthropods, in particular insects and ticks in an individual, the method comprising the step of applying a composition according to embodiments 1-30 to the individual, wherein application of the composition repels a mosquito, sand fly (or an insect) and other blood-sucking arthropods from the individual, thereby reducing bites for a blood-meal.

32. The method according to embodiment 31, wherein application of the composition is by topical administration.

33. A method of reducing a mosquito infestation to a location, the method comprising the steps of applying a composition according to embodiments 1-30 to the location, wherein the application repels insects and/or arachnids, in particular mosquitoes, sand flies and/or ticks from the location, thereby reducing the infestation.

34. The method according to embodiment 33, wherein the location is a plant or group of plants, a particular area of land, or a man-made structure.

35. The method according to embodiment 33, wherein the man-made structure is a commercial building, a house, a shed, a livestock maintenance area, other physical structure, or any part thereof.

36. A compound or composition having a repellency activity with respect to blood-sucking arthropods, in particular insect and/or arachnid repellent activity, preferably mosquito repellency activity, wherein the compound binds to *Anopheles gambiae* OBP1, OBP3, OBP4, OBPS, OBP20, OBP47, and/or or one or more different mosquito OBPs.

37. The compound or composition according to embodiment 35, wherein presence of the composition repels blood-sucking arthropods, in particular insect and/or arachnids, for example mosquitoes by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, as compared to not having the composition present.

38. The compound or composition according to embodiment 35 or 36, wherein the composition reduces an interaction between blood-feeding arthropod, such as a blood-feeding insect and/or arachnid, and a mammal or bird, in particular a mosquito-mammalian host interaction.

39. The compound or composition according to embodiment 37, wherein the composition reduces interaction of said blood-feeding arthropod with a mammal or bird by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

40. The compound or composition according to embodiments 35-38, wherein the composition reduces an ability of a blood-feeding arthropod, in particular an insect and/or arachnid, such as a mosquito to obtain a blood meal from a mammal or a bird.

41. The compound or composition according to embodiment 39, wherein the composition reduces an ability of said blood-feeding arthropod, in particular said mosquito to obtain a blood-meal from a mammal or bird by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, compositions, traps, methods or uses of repellents for mosquitoes and other blood-sucking arthropods.

Example 1

Purification of Essential Oils from Plant Material

This example illustrates how to extract an essential oil from plant material.

To extract an essential oil from a plant, material was collected from mostly aromatic plant species. Essential oils were obtained by steam-distilling 50-70 g of plant samples (examples are shown in Table 1) for 4 hours in a modified Clevenger distillation apparatus equipped with a water-cooled oil receiver to reduce hydrodistillation artifacts. The volatiles, which were carried by water vapor, were condensed and trapped in a layer of diethyl ether. The ether layer was dried over magnesium sulfate to remove residual water, concentrated under a gentle stream of nitrogen and each essential oil was stored at −20° C.

TABLE 1

Plant Species and Parts Used to Extract Essential Oils (EOs)

| EO No. | Species Code | Species | Part used |
|---|---|---|---|
| 1 | Lam27 | *Salvia sclarea* | flowers |
| 3 | Lam12 | *Lavandula stoechas* | aerial plant |

TABLE 1-continued

Plant Species and Parts Used to Extract Essential Oils (EOs)

| EO No. | Species Code | Species | Part used |
|---|---|---|---|
| 5 | Lam22.1 | *Coridothymus capitatus* | aerial plant |
| 6 | Lam05.4 | *Origanum majorana* | aerial plant |
| 9 | Lam23 | *Origanum heracleoticum* | aerial plant |
| 11 | Lam09.1 | *Salvia fruticosa* | aerial plant |
| 14 | Lam07.2 | *Origanum vulgare* | flowers |
| 16 | Lau02 | *Cinamomum camphora* | leaves |
| 20 | Ana02 | *Schinus* cf. *molle* | leaves |
| 21 | Com01 | *Santolina chamaecyparissus* | aerial plant |
| 29 | Gut02 | *Hypericum* sp. | leaves |
| 36 | Gut01 | *Hypericum balearicum* | aerial plant |
| 41 | Cup04 | *Juniperus foenicae* | shoots |
| 46 | Lam02 | *Rosmarinus officinalis* | aerial plant |
| 47 | Lam28 | *Ocimum basilicum* | aerial plant |
| 54 | Myr02 | *Eucalyptus camaldulensis* | leaves |
| 55 | Pin03 | *Pinus halepensis* | shoots |
| 166 | Rut08 | *Citrus sinensis* | fruit peel |
| 169 | Lam07 | *Origanum* sp. | aerial plant |
| 171 | Lam01 | *Satureja thymbra* | aerial plant |
| 174 | Car02 | *Dianthus caryophyllus* | dry seeds |
| 176 | Ill01 | *Illicium verum* | dry fruits |
| 180 | Umb08 | *Cuminum cyminum* | dry seeds |
| 181 | Umb09 | *Pimpinella anisum* | dry seeds |
| 189 | Cup05 | *Juniperus* sp. | dry fruits |
| 190 | Umb10 | *Carum carvi* | dry seeds |

Example 2

Screening of Essential Oils Using a OBP Binding Competition Assay

To identify a mosquito repellent disclosed herein, essential oils were first screened for candidate compounds based upon the ability of that compound to bind mosquito OBPs using a fluorescent binding competition assay. The fluorescence binding competition assay employed in the identification of candidate compounds was based on displacement of the fluorescent probe N-phenyl-1-naphthylamine (1-NPN) from an OBP by various compounds present in the purified essential oils.

To construct an expression construct comprising an OBP, a full-length cDNA for an OBP was subcloned into a pIE1/153A expression vector [Farrell et al (1998). High-level expression of secreted glycoproteins in transformed lepidopteran insect cells using a novel expression vector. *Biotechnol Bioeng* 60(6): 656-663; Lu et al (1997). A baculovirus (Bombyx mori nuclear polyhedrosis virus) repeat element functions as a powerful constitutive enhancer in transfected insect cells. *J Biol Chem* 272(49): 30724-30728] in a manner that enabled C-terminal tagging of the expressed OBPs with a 6×His purification and a c-Myc epitope tag as previously described [Douris et al (2006). Stably transformed insect cell lines: tools for expression of secreted and membrane-anchored proteins and high-throughput screening platforms for drug and insecticide discovery. *Adv Virus Res* 68: 113-156]. pIE1/153A expression constructs (pIE1/153A.OBPx) were made using the following polynucleotide sequences: OBP1 (SEQ ID NO: 1), OBP3 (SEQ ID NO: 2), OBP4 (SEQ ID NO: 3), OBP5 (SEQ ID NO: 4), OBP20 (SEQ ID NO: 5) and OBP47 (SEQ ID NO: 6). These six OBPs were selected since each is highly expressed in the antennae of *A. gambiae* with a strong female bias [Biessmann et al (2002). Isolation of cDNA clones encoding putative odorant binding proteins from the antennae of the malaria-transmitting mosquito, *Anopheles gambiae*. *Insect Mol Biol* 11(2): 123-132].

To generate a transiently transformed cell line, weekly subcultured HIGHFIVE™ cells (Invitrogen, Inc., Carlsbad, Calif.), grown at 28° C. in either IPL-41 insect cell culture medium (Genaxxon Biosciences) supplemented with 10% fetal bovine serum (Life Technologies, Inc., Carlsbad, Calif.) or serum free ESF 921 medium (Expression systems LLC), were transfected with a pIE1/153A expression construct using Lipofectin (Invitrogen, Inc., Carlsbad, Calif.) or Escort IV reagents (Sigma, St. Louis, Mo.) according to the manufacturers' instructions. To generate a stable transformed cell line, HIGHFIVE™ cells were co-transfected with a pIE1/153A expression construct and pEApac, [Douris et al (2006). Stably transformed insect cell lines: tools for expression of secreted and membrane-anchored proteins and high-throughput screening platforms for drug and insecticide discovery *Adv Virus Res* 68: 113-156], a plasmid conferring resistance to puromycin, at a molar ratio of 100 pIE1/153A.OBPx to 1 pEApac. Transformed cell lines were selected within a period of 2-3 weeks and maintained in the appropriate growth medium in the presence of 50 µg/mL gentamycin (Invitrogen, Inc., Carlsbad, Calif.) and 15 or 50 µg/ml puromycin (Sigma, St. Louis, Mo.).

To express and purify an OBP, 500 mL cultures of transformed cells were grown in a BIOWAVE® 2SPS bioreactor (Wave Biotech AG, Switzerland) for 7-8 days to a cell density of about $2 \times 10^6$ cells/mL in serum containing or about $7 \times 10^6$ cells/mL in serum free medium. Culture supernatants were collected, pH adjusted to 8.0 using 0.5 M sodium phosphate buffer (pH 8.0) and batch bound overnight to Ni-NTA agarose resin (Qiagen Inc., Valencia, Calif.). The resin was poured into a column and then washed once with with 200 mL of 10 mM imidazole in 50 mM phosphate buffer (pH 8.0) containing 300 mM NaCl and then washed once with 100 mL of 20 mM imidazole in 50 mM phosphate buffer (pH 8.0) containing 300 mM NaCl. Protein was eluted with 250 mM imidazole in 50 mM phosphate buffer (pH 8.0) containing 300 mM NaCl. Protein samples from all fractions were analyzed on 15% sodium dodecyl sulphate (SDS)-polyacrylamide gels, stained with silver nitrate and also electroblotted on nitrocellulose membranes for visualization by Western Blot analysis using the antibodies against the c-Myc tag (Santa Cruz, Biotechnology Inc., Santa Cruz, Calif.) and ECL detection (Amersham Pharmacia Biotech). OBP containing fractions were concentrated and loaded onto a Superdex75 gel filtration column (GE Healthcare) equilibrated with 10 mM Tris-HCl pH 8.0 containing 200 mM NaCl, and the corresponding peak of protein eluted was identified by SDS-PAGE analysis. Fractions were subsequently subjected to buffer exchange in 10 mM Tris-HCl pH 8.0, 50 mM NaCl, using Amicon Ultra-15 Centrifugal filter Devices (Millipore).

To conduct a fluorescence binding competition assay, the concentration of each purified OBP required for maximal binding of 1-NPN was first determined in binding assays using increasing OBP amounts. All tested OBPs bound 1-NPN at about 1:1 molar ratios. Essential oils were then tested for binding using the minimum amount of each purified OBP that yielded maximal binding of the fluorescent probe. Each essential oil was added at a defined dilution ranging from 1/12,500 to 1/100,000. The probe was excited at 337 nm and emission spectra were recorded between 386-460 nm (peak emission in the presence of an OBP was between 402-406 nm). Emission spectra were recorded on an Infinite M-200 fluorimeter (Tecan Trading AG, Switzerland). For Kd value calculations, the dissociation constant of 1-NPN (Kp) was determined by fluorescence measurements of solutions containing OBP and 1-NPN. Bound candidate compound concentration was calculated from the fluorescence intensities assuming 100% functional protein and an 1:1 [OBP]:[1-NPN] stoichiometry at saturation. The Kd was calculated using a non-linear-regression data analysis program (GraFit).

The results shown in Table 2 indicate that of 26 essential oils examined, 11 contained at least one compound which competed with 1-NPN for binding to one or more of the tested OBPs, while the remaining 15 essential oils appeared not to have any compounds that could displace 1-NPN from any of the tested OBPs (Table 2). For the essential oils listed in table 2, when an oil contained one or more compounds that bound to several OBPs, displacement of 1-NPN ranged from 11% to 46%. The binding experiments also identified OBP4 as the protein with the most promiscuous binding behavior (Table 2).

TABLE 2

Binding Activity of Essential Oils (EOs) and Their Fractions (a, b, c) to OBPs

| EO No | Species Code | OBP1 | OBP3 | OBP4 | OBP5 | OBP20 | OBP47 | Max % OBP binding |
|---|---|---|---|---|---|---|---|---|
| 1 | Lam27 | — | — | — | — | — | — | 0% |
| 3 | Lam12 | — | — | — | — | — | — | 0% |
| 5 | Lam22.1 | — | ✓ | ✓ | — | ✓ | — | 21% |
| 6 | Lam05.4 | — | — | — | — | ✓ | — | 17% |
| 9 | Lam23 | — | — | ✓ | — | ✓ | — | 19% |
| 9b | | — | ND | ND | — | ✓ | ✓ | 22% |
| 9c | | — | ND | ND | — | ✓ | ✓ | 26% |
| 11 | Lam09.1 | — | — | — | — | — | — | 0% |
| 14 | Lam7.2 | ✓ | — | ✓ | — | ✓ | — | 28% |
| 16 | Lau02 | — | — | — | — | — | — | 0% |
| 20 | Ana02 | — | — | — | — | — | — | 0% |
| 21 | Com01 | ✓ | ✓ | ✓ | ✓ | ✓ | ✓ | 25% |
| 21b | | ✓ | ✓ | ✓ | ✓ | ✓ | ✓ | 43% |
| 21c | | ✓ | ✓ | ✓ | ✓ | ✓ | ✓ | 39% |
| 29 | Gut02 | ✓ | ✓ | — | ✓ | — | ✓ | 12% |
| 29b | | ✓ | — | ✓ | ✓ | — | ND | 23% |
| 29c | | ✓ | ✓ | ✓ | ✓ | ✓ | ND | 24% |
| 36 | Gut01 | — | — | — | — | — | — | 0% |
| 41 | Cup04 | — | — | — | — | — | — | 0% |
| 46 | Lam02 | — | — | — | — | — | — | 9% |
| 47 | Lam28 | ✓ | ✓ | ✓ | ✓ | ✓ | ✓ | 46% |
| 47a | | ✓ | ✓ | ✓ | ✓ | ✓ | ND | 39% |
| 47b | | ✓ | ✓ | ✓ | ✓ | ✓ | ND | 60% |
| 47c | | — | — | ✓ | ✓ | — | ND | 21% |
| 54 | Myr02 | ✓ | ✓ | — | ✓ | — | — | 11% |
| 55 | Pin03 | — | — | — | — | — | — | 5% |
| 166 | Rut08 | — | — | — | — | — | — | 0% |
| 169 | Lam07 | — | — | ✓ | — | — | — | 35% |
| 171 | Lam01 | — | — | — | — | — | — | 0% |
| 174 | Car02 | — | — | — | — | — | — | 0% |
| 176 | Ill01 | — | — | — | — | — | — | 0% |
| 180 | Umb08 | ✓ | ✓ | — | ✓ | ✓ | ✓ | 21% |
| 180a | | — | — | ✓ | ✓ | — | — | 13% |
| 180b | | ✓ | ✓ | ✓ | ✓ | ✓ | ✓ | 44% |
| 180c | | ✓ | ✓ | ✓ | ✓ | ✓ | ✓ | 81% |
| 181 | Umb09 | — | — | — | — | — | — | 0% |
| 189 | Cup05 | — | — | — | — | — | — | 0% |
| 190 | Umb10 | ✓ | — | ✓ | ✓ | ✓ | ✓ | 34% |
| 190b | | ✓ | ✓ | ✓ | ✓ | ✓ | ND | 17% |
| 190c | | ✓ | — | ✓ | ✓ | ✓ | ND | 24% |

✓, binding competition (>9%);

—, no binding competition;

ND, not done;

a, b, c designations, see example 4 description.

Example 3

Testing of Essential Oils Containing OBP Binding Compounds Using a Repellence Assay To test the behavior of female mosquitoes to an essential oil containing OBP binding components, a previously described repellence assay [Kröber et al. (2010). An In Vitro Assay for Testing Mosquito Repellents Employing a Warm Body and Carbon Dioxide as a Behavioral Activator. Journal of the American Mosquito Control Association 26(4) 381-386] was conducted that measures the number of mosquito landings on a warm surface onto which an essential oil containing at least one candidate compound was applied.

To conduct a repellency assay, a selected essential oil or ethanol negative control was applied to a warm body at a dose of about 3.8 µg/cm$^2$ and allowed to dry for 40 seconds in order to allow evaporation of the solvent before introduction into the test cage with mosquitoes. As positive control for repellence, DEET dissolved in ethanol was applied to the warm body at the same dose. The treated warm body in conjunction with a pulse of carbon dioxide was introduced into the test cage containing fifty *Anopheles gambiae* (Giles) ss strain 16CSS female mosquitoes that were 4-11 days old and the number of mosquito landings on the warm body occurring within a 2-minute period was counted. Each candidate compound was tested in five different cages (i.e., 250 female mosquitoes) in a randomized design, and the ethanol control and up to four candidate compounds were tested in each cage. Raw data on numbers of landings by mosquitoes were analyzed using a linear mixed model accounting for treatment, experimental day, the individual cage, the number of females per cage and the level of the carbon dioxide pulse in ppm using R (R Development Core Team, 2010) and the packages LME4 (Bates and Maechler, lme4: Linear mixed-effects models using {S4} classes.{R} package version 0.999375-32, 2009) and NLME (Pinheiro et al, nlme: Linear and Nonlinear Mixed Effects Models, 2010; the R Development Core Team, R: A Language and Environment for Statistical Computing, 2010). Repellent values were calculated from counted landings on treatments versus the overall landings on pooled controls.

The results of the tests on 26 of the essential oils shown in Table 1 indicate that of the 11 essential oils competing with 1-NPN for binding to one or more OBPs (Table 2), 5 displayed very strong repellent activities in the warm body assay at a dose of 3.8 mg/cm$^2$ (Table 3). Essential oils extracted from *Coridothymus capitatus, Origanum majorana, Origanum heracleorticum, Origanum vulgare* and *Origanum* sp. exhibited repellency well above 90%, similar to the activity displayed by DEET, a known repellent, at the same dose (Table 3). The results also revealed that an additional essential oil, that of *Santolina chamaecyparissus*, displayed lower but still moderate repellent activity (median repellence of 72%). Warm body tests with the 15 essential oils that failed to bind to any of the six OBPs tested to any measurable degree showed that only one "OBP binding-negative" essential oil, that of *Dianthus caryophyllus*, had moderate repellent activity (median repellence of 74%).

TABLE 3

Repellence Activity of Essential Oils (EO) and their Fractions (a, b, c)

| EO | Fraction | Species | Rep Median % | P value control | P value DEET |
|---|---|---|---|---|---|
| 1 | | *Salvia sclarea* | 33 | 0 | 0 |
| 3 | | *Lavandula stoechas* | 48 | 0 | 0 |
| 5 | | *Coridothymus capitatus* | 97 | 0 | 0.89 |
| 6 | | *Origanum majorana* | 95 | 0 | 0.88 |
| 9 | | *Origanum heracleoticum* | 93 | 0 | 0.49 |
| | 9b | | 101 | 0 | 0.77 |
| | 9c | | 95 | 0 | 0.72 |
| 11 | | *Salvia fruticosa* | 23 | 0.01 | 0 |
| 14 | | *Origanum vulgare* | 95 | 0 | 0.82 |
| 16 | | *Cinamomum camphora* | 12 | 0.12 | 0 |
| 20 | | *Schinus* cf. *molle* | 29 | 0 | 0 |
| 21 | | *Santolina chamaecyparissus* | 72 | 0 | 0.01 |
| | 21b | | 36 | 0 | 0 |
| | 21c | | 9 | 0.24 | 0 |
| 29 | | *Hypericum* sp. | 38 | 0 | 0 |
| | 29b | | 48 | 0 | 0 |
| | 29c | | 83 | 0 | 0.17 |
| 36 | | *Hypericum balearicum* | 34 | 0 | 0 |
| 41 | | *Juniperus foenicae* | 28 | 0 | 0 |
| 46 | | *Rosmarinus officinalis* | −7 | 0.54 | 0 |
| 47 | | *Ocimum basilicum* | 14 | 0.01 | 0 |
| | 47a | | 49 | 0 | 0 |
| | 47b | | 24 | 0 | 0 |
| | 47c | | 30 | 0.03 | 0 |
| 54 | | *Eucalyptus camaldulensis* | 22 | 0 | 0 |
| 55 | | *Pinus halepensis* | 32 | 0 | 0 |
| 166 | | *Citrus sinensis* | 28 | 0 | 0 |
| 169 | | *Origanum* sp. | 93 | 0 | 0.66 |
| 171 | | *Satureja thymbra* | 6 | 0.50 | 0 |
| 174 | | *Dianthus caryophyllus* | 74 | 0 | 0.01 |
| 176 | | *Illicium verum* | 26 | 0 | 0 |
| 180 | | *Cuminum cyminum* | 7 | 0.39 | 0 |
| | 180a | | 4 | 0.62 | 0 |
| | 180b | | 25 | 0 | 0 |
| | 180c | | 66 | 0 | 0 |
| 181 | | *Pimpinella anisum* | 41 | 0 | 0 |
| 189 | | *Juniperus* sp. | 37 | 0 | 0 |
| 190 | | *Carum carvi* | 45 | 0 | 0 |
| | 190b | | 29 | 0 | 0 |
| | 190c | | 64 | 0 | 0 |

Example 4

Screening of Essential Oil Fractions Using an OBP Binding Competition and Repellency Assay Since the tested essential oils are complex mixtures of different chemical compounds, both binding activity data and behavioral effects may be affected by low concentrations of active compounds in each essential oil, possible functional interference interactions between compounds, or a combination of both effects. As such, both binding activity and behavioral assays were repeated on fractions of selected essential oils.

Essential oils purified in Example 1 were further fractionated using solid phase extraction (SPE) on SEP-PAK® Plus Alumina A (Waters) and eluting at a velocity of 1 drop/second with the following solvents in sequence: Fraction A, 3 mL pentane; Fraction B 6 mL pentane/diethyl ether 90:10; and Fraction C, 3 mL diethyl ether. Each fraction was concentrated under a gentle stream of nitrogen and stored at −20° C. until use. The fluorescence binding competition assay was performed as described in Example 2.

Ten essential oils were separated into three fractions and each fraction tested in the fluorescence binding competition assay as described in Example 2. The results indicate that fractions from at least seven of the essential oils examined appeared enriched for at least one compound which competed with 1-NPN for binding to one or more of the tested OBPs (Table 2). Of those oil fractions that had a compound that could compete with 1-NPN, the percent displacement ranged form about 13% to about 81%.

Fractions from 6 selected essential oils were also tested using the repellence assay as described in Example 3. The analysis of these fractions revealed that fractionation resulted in enrichment of bioactive components or removal of competing inhibitory bioactivities from the fractions displaying enhanced repellent activities or both. For example, essential oil of *Cuminum cyminum*, which was inactive in the warm body assay (median repellency of 7%), showed that fraction 108 C was found to possess significant repellent activity (median repellency of 66%; Table 3). As another example, essential oil of *Santoline chamaecyparissus* was found to be more active than any of the fractions derived from it (Table 3), a finding suggesting possible combinatorial effects amongst two or more bioactive components partitioning in the different fractions.

Example 5

Candidate Compound Identification Using Gas Chromatography-Linked Electroantennogram Recordings and Mass Spectrometry In order to identify compounds present in essential oils with mosquito repellent activity, selected essential oils exhibiting affinity to OBPs and repellent activity in mosquitoes were subjected to gas chromatography-coupled electroantennogram (GC-EAG) analysis (FIG. 1) and individual compounds eliciting strong EAG responses were analyzed by gas chromatography-coupled mass spectrometry (GC-MS).

Electrophysiological recordings from whole mosquito antenna: Coupling EAG recordings from an *A. gambiae* antenna to the effluent of a high-resolution gas chromatographic (GC) column permitted the determination of the elution profiles of biologically active components of essential oils showing repellence. Recordings were made from to 4-9 day-old female mosquitoes. The head was excised at the occipital opening and placed on the reference glass electrode containing Hayes mosquito Ringer [Hayes (1953). Determination of a physiological saline for *Aedes aegypti* (L.). *J Econ Entomol* 46: 624-627] mounted in a humidified airstream (90-98% RH; Guerin and Visser (1980). Electroantennogram Responses of the Carrot Fly, *Psila rosae*, to Volatile Plant Components. *Physiological Entomology* 5(2): 111-119] and its antenna exposed to compounds eluting from the GC column (Biessamann et al. (2010). The *Anopheles gambiae* odorant binding protein 1 (AgamOBP1) mediates indole recognition in the antennae of female mosquitoes. *PLoS One* 5(3): e9471]. The EAG response was recorded via a glass electrode filled with Kaissling sensillum lymph Ringer [Kaissling (1995). Single unit and electroantennogram recordings in insect olfactory organs. In Experimental Cell Biology of Taste and Olfaction. Current Techniques and Protocols, Spielman AIaB, J. G. (ed), 361-386. Boca Raton, Fla.: CRC Press] brought into contact with the terminal antennal segment whose tip was cut off. Only antennae showing an EAG response at least double the noise level to a 1 ml puff of air over 1 μg geranylacetone in a 5 ml stimulus syringe were used for recording EAG responses to the essential oils.

To conduct a GC-EAG analysis, about 2 μg of an essential oil was injected in 1-3 μL of dichloromethane (DCM) onto an apolar capillary column (95% dimethyl polysiloxan with 5% diphenyl polysiloxan, 15 m long, 0.25 mm i.d., 0.10 μm film thickness; BGB Analytik, Switzerland) installed in a 5300 Carlo Erba Instruments chromatograph. Hydrogen was used as carrier gas with the oven held at 40° C. for 3 minutes then heated up 25° C./min to 230° C. and held at the final temperature for 15 min. The column effluent was split (50:50) between the flame ionization detector (FID) of the chromatograph and the mosquito antennal preparation. The EAG signal was fed into an AC/DC amplifier (×100) via a high impedance preamplifier (×10), recorded on the hard disk of a PC via a 16-bit analogue-digital IDAC4 interface (Syntech, Netherlands) and monitored simultaneously with an oscilloscope (Tektronix 5103, USA). Kovats retention indices (Kis) were calculated for the EAG-active compounds present in the extracts and fractions. FIG. 1 illustrates the results obtained using the GC-EAG analysis.

This analysis resulted in the identification of a number of compounds that were capable of triggering EAG responses in female *A. gambiae* antennae. These included carvacrol, β-caryophyllene, (E)-methyl-cinnamate, cumin alcohol, cumin aldehyde, cuminic acid, p-cymene, linalool, α-pinene, β-pinene and safranal, and γ-terpineol.

To conduct a GC-MS analysis, 1 μL of an essential oil extract or fraction thereof was dissolved in 1 mL of DCM and 1 μL of this solution was analyzed on an Agilent 7890A GC apparatus coupled with a mass selective detector (5975E MSD) and equipped with a Gerstel MPS2XL autosampler. The GC was equipped with a Zebron ZB-5 capillary column (30 m×0.25 mm i.d. coated with 5% diphenyl-95% dimethylpolysiloxane, 0.10 μm thickness). The injection port and transfer line were set at 250° C. with helium as carrier gas (at 9.59 psi). Oven temperature was first increased from 40° C. to 150° C. at 5° C./min, then to 220° C. at 10° C./min and then to 310° C./min at 30° C./min and held for 8 minutes. Mass spectra were acquired in EI mode (at 70 eV). A set of $C_{10}$-$C_{24}$ alkanes was injected under the same experimental conditions and KIs were calculated for the compounds present in the plant extracts. Both the recorded mass spectra and the KIs were compared with those reported in electronic libraries Nist 0.5, Wiley7, and Adams. Elution profiles were compared to those obtained from the GC-EAG recordings (above), and KIs of single compounds were compared taking into account the slight differences observed due to the use of different carrier gases, so as to identify compounds eliciting EAG responses from the mosquito antennae.

Example 6

Testing of Candidate Compounds Using a Repellence Assay

To test the behavior of female mosquitoes to a candidate compound identified in Example 5, behavioral assays were made using the identified compounds. The repellent assay was performed as described in Example 3, except that candidate compounds were dissolved in ethanol and tested initially at doses between 1.0 and 5.0 μg/cm$^2$ (about 5-31.5 nmole/cm$^2$) and, whenever necessary, at lower and/or higher doses as well. Besides the compounds identified in Example 5, compounds related to these were also tested including ethyl-cinnamate and butyl-cinnamate (Table 4).

TABLE 4

Repellence Activity of Compounds Identified in Essential Oils and Related Compounds Compounds identified in Essential Oils (EOs)

| CAS # | Full name | Essential Oil/Fraction | nmole per cm² | Median Repellency (%) | P value compared to ethanol control | P value compared to DEET* |
|---|---|---|---|---|---|---|
| 134-62-3 | DEET | | 20 | 98.5 | 0 | ref |
| 499-75-2 | carvacrol | 169, 5, 14, 169 | 25 | 93.3 | 0 | 0.509 |
| 1754-62-7 | methyl-trans-cinnamate | 47, 47a, 47b | 20 | 14.0 | 0.001 | 0 |
| 536-60-7 | cumin alcohol | 180, 180c | 20 | 92.3 | 0 | 0.121 |
| 122-03-2 | cumin aldehyde | 180, 180a, 180b, 180c | 20 | 13.5 | 0.0016 | 0 |
| 536-66-3 | cuminic acid | 180, 180b, 180c | 20 | 74.2 | 0 | 0.706 |
| 89-83-8 | thymol | 5, 169 | 31.5 | 89.7 | 0 | 0.203 |

Related Compounds

| CAS # | Full name | Related compound | nmole per cm² | Median Repellency (%) | P value compared to ethanol control | P value compared to DEET* |
|---|---|---|---|---|---|---|
| 103-36-6 | (E)-ethyl-cinnamate | (E)-methyl-cinnamate | 20 | 82.8 | 0 | 0.4238 |
| 538-65-8 | butyl-cinnamate | (E)-methyl-cinnamate | 20 | 88.7 | 0 | 0.1461 |

*Statistically significant differences are those with P values <0.05

The results, which are summarized in Table 4, show that carvacrol, thymol, cumin alcohol and cuminic acid are repellents with activity comparable to DEET. Compounds such as (+) and (−) carvone, β-caryophyllene, E-methyl-cinnamate and cuminaldehyde, (+) and (−) limonene, α- and β-pinene, γ-terpinene and safranal displayed only weak or no repellent activity at all in the warm body assay. Interestingly, linalool and p-cymene exhibited properties suggesting attractant activity consistent with the behavioral effects exerted by fractions relative to the parent essential oils.

Compounds related to (E)-methyl-cinnamate, which were also assessed for activity in the warm body assays due to their structural similarity with the identified cinnamate, proved to be much stronger repellents than methyl-cinnamate. Thus, in contrast to the methyl cinnamate, which displayed only marginal repellent activity (median repellency of 14%; Table 4), ethyl-cinnamate, and butyl-cinnamate were found to have, at comparable doses, repellencies ranging from 82.8% and 88.7%, respectively, indicative of an effect of the extended hydrophobic chain (Table 4).

Example 7

Testing of Repellent Compound Combinations Using a Repellence Assay

To test the behavior of female mosquitoes to various combinations of candidate compounds identified in Example 6, repellence assays were made as in Example 3. These repellent assays were made to compare the effectiveness of the strongest repellent compounds identified in Example 6, including, without limitation, carvacrol, ethyl cinnamate, butyl cinnamate, and cumin alcohol with that of DEET.

Figure 2:
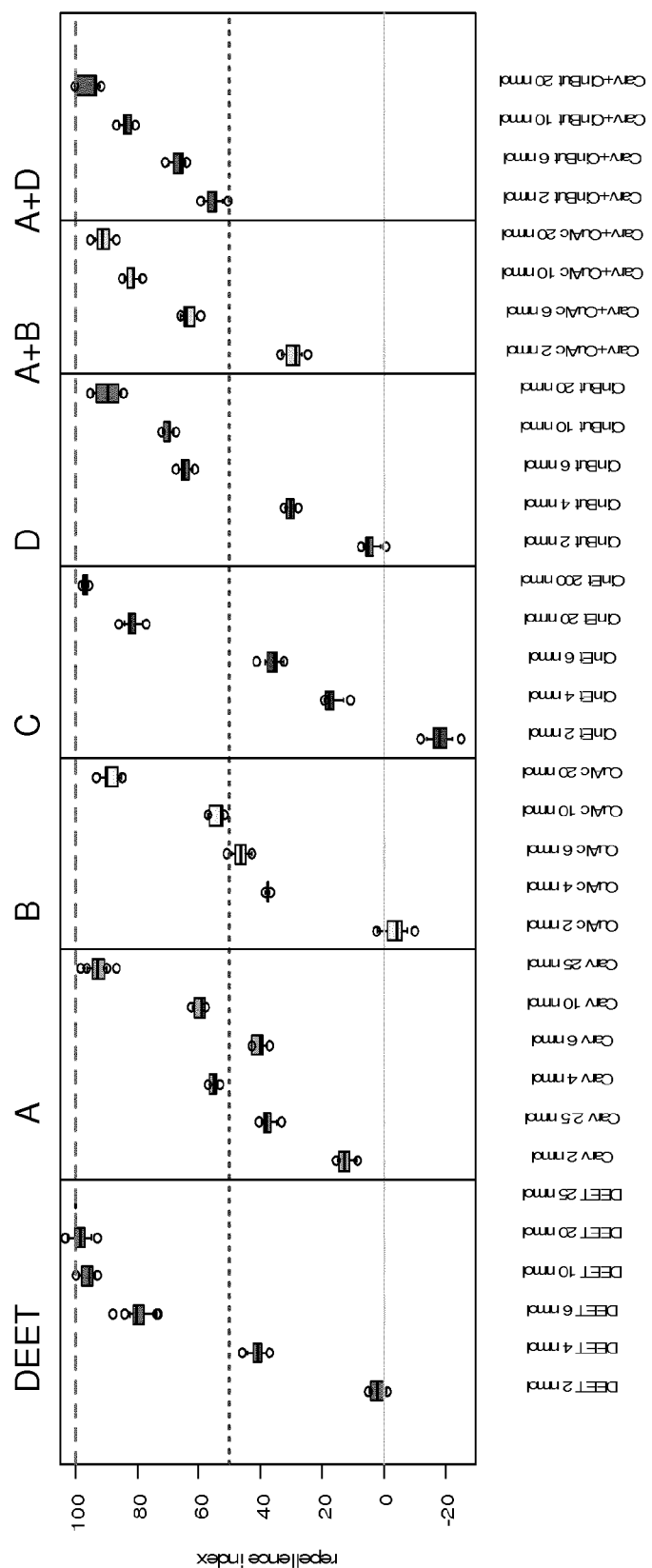
FIG. 2 shows the repellence index of compositions comprising different compounds in accordance with embodiments of the invention, compared to a reference compound (DEET), each compound or combination of compounds (carvacrol+cumin alcohol, and carvacrol+butyl-cinnamate) being applied at different increasing concentrations as indicated at the bottom of the figure. Compounds are: A: carvacrol (Cary), B: cumin alcohol (CuAlc), C: ethyl-cinnamate (CinEt), and D: butyl-cinnamate (CinBut).

The results indicate that all compounds tested on their own showed a strong increase in repellent activity by increasing the dose from 2 to 20 nmol/cm² (Table 5 and FIG. 2). In addition, individually, all compounds showed strong repellent activity at 20 nmole/cm², although DEET was somewhat more repellent. In addition, carvacrol retained repellent activity at a concentration as low as 2 nmole/cm². These results also showed that all mixtures containing cavacrol showed a strong increase in repellence with increasing dose (Table 5 and FIG. 2). Furthermore, equimolar binary mixtures of carvacrol with each of the other two compounds at a total concentration of 2.0 nmole/cm² were significantly more effective than any of the individual compounds alone, including DEET, at the same final concentration, (P≤0.05). In addition, a binary mixture of butyl cinnamate and cumin alcohol also showed an increase in repellence with increasing dose (Table 5).

TABLE 5

Dose-response repellence of Anopheles gambiae to selected compounds and their mixtures compared to DEET

| Compound or compound mixture | Median repellence % | | | | | |
|---|---|---|---|---|---|---|
| | 2 nmol | 4 nmol | 6 nmol | 10 nmol | 20 nmol | 25 nmol |
| DEET | 2 | 41 | 80 | 96 | 98 | 100 |
| Carvacrol | 13 | 55 | 40 | 59 | — | 93 |
| Cumin alcohol | −4 | 38 | 46 | 53 | 93 | — |
| (E)-ethyl-cinnamate | −18 | 18 | 35 | — | 83 | — |
| Butyl-cinnamate | −1 | 28 | 61 | 68 | 89 | — |

TABLE 5-continued

Dose-response repellence of Anopheles gambiae to selected compounds and their mixtures compared to DEET

| Compound or compound mixture | Median repellence % | | | | | |
|---|---|---|---|---|---|---|
| | 2 nmol | 4 nmol | 6 nmol | 10 nmol | 20 nmol | 25 nmol |
| Carvacrol + Cumin alcohol | 28 | — | 64 | 81 | 91 | — |
| Carvacrol + Butyl-cinnamate | 55 | — | 66 | 84 | 94 | — |
| Cumin alcohol + Butyl-cinnamate | 7 | 25 | — | 74 | 94 | — |

FIG. 2. graphically shows repellence indices (predicted values from generalized linear mixed model) of binary mixtures of carvacrol (Cary) (A), cuminic alcohol (CuAlc) (A+B) and butyl cinnamate (CinBut) (A+D) at different doses on the warm body for *Anopheles gambiae* females as compared to different doses of carvacrol (A), cumin alcohol (B), ethyl cinnamate (CinEt) (C), butyl cinnamate (D) and DEET presented singly. The doses tested were 2, 4, 6 10 and 20 nmol/cm$^2$ for the single compounds. The binary 50:50 mixtures were tested at 2, 6, 10 and 20 nmol/cm$^2$, with each compound making up half the amount tested, so that, for example, the 2 nmol/cm$^2$ concentration in column A+B represents 1 nmol/cm$^2$ of A and 1 nmol/cm$^2$ of B in a binary mixture. DEET was also tested at 25 nmol (top response) and carvacrol was tested at the additional dose of 2.5 nmol (second from left within its column). As an indication, DEET at 20 nmol/cm$^2$=3.8 μg/cm$^2$. Mosquitoes were activated using a puff of $CO_2$ from a gas tank upon introduction of the warm body into the test cage containing 50±5 *A. gambiae* females and mosquito landings were counted for 2 minutes. Each treatment (dose) was tested using five test cages, i.e. on a total of 250 female *A. gambiae*. The limits of the boxes indicate the twenty-fifth and seventy-fifth percentiles, the solid line in the box is the median, the capped bars indicate the tenth and the ninetieth percentiles, and data points outside these limits are plotted as circles.

Ternary mixtures were also tested at a total concentration of 2 nmol/cm$^2$ and achieved effects that were similar to those obtained with the binary mixtures. (Results not shown in Table 5 and FIG. 2).

Example 8

Spatial Repellent Effect of Compound Carvacrol

Carvacrol was tested in a wind tunnel (60×60×20 cm) in order to test for inhibition of the attractiveness of dirty socks, which are otherwise very attractive to the malaria mosquito *A. gambiae*. Experiments were conducted at 25° C. and 80% relative humidity at a wind speed of 0.5 m·s$^{-1}$ during the last 6 hours of scotophase. Dim fluorescent light (4 Lux) was provided from above (Philips TLD, 32 Watts at 36 KHz). A tube (55 mm inner diameter) was covered at its downwind end with mosquito netting which was treated with 38 or 57 μg DEET/cm$^2$ or 38 or 76 μg carvacrol/cm$^2$ or the solvent (ethanol) alone (control). Groups of 30 *A. gambiae* females were released from a release cage at the downwind end of the wind tunnel and their landing behaviour on the mosquito netting was recorded with a high definition video camera. The number of mosquitoes landing on the mosquito netting over 5 minutes was counted.

Whereas landings by *A. gambiae* females on the netting downwind of the sock was high in controls, the mosquito netting treated with either DEET or carvacrol clearly inhibited *A. gambiae* females from landing on the downwind end of the tube containing the dirty sock (Table 6).

TABLE 6

Spatial repellence effect of compound carvacrol compared to DEET

| Compound | μg/cm$^2$ | nmol/cm$^2$ | Mean Landings/ 5 minutes |
|---|---|---|---|
| Control | 0 | 0 | 24.6 |
| DEET | 38 | 200 | 0 |
| DEET | 57 | 300 | 0 |
| Carvacrol | 38 | 250 | 0 |
| Carvacrol | 76 | 500 | 0 |

Example 9

Field Testing of Spatial Repellent Effects of Compounds

To test the effects of repellent compounds or compositions disclosed herein on mosquitoes in a controlled environment resembling actual living quarters and conditions, field trials with standardized experimental huts were conducted at Kainji Dam in North Central Nigeria.

Six such huts were built in a straight line, and the distance between huts was 11 meters. These huts follow a traditional square design, the walls are built with concrete blocks that are subsequently plastered with cement, each wall has a window. The ceiling is plywood and the roof is thatched with eaves that are open, thereby allowing free flow of air into and out of the hut, and thus entry and exit of mosquitoes. There is a door for entry and exit. Two opposing sides of each but have window exit traps and screened verandas to capture mosquitoes leaving via the windows or eaves. Each but is raised off the ground on a concrete platform and surrounded by a moat filled with water in order to prevent ants from entering. Each but is fitted with a mattress and an untreated bed net for sleepers. These huts are similar in design and concept to those used previously elsewhere for studying mosquito behavior and measuring the efficacy of various mosquito control products or intervention methods in Tanzania and Gambia. For design parameters refer to WHOPES 2005. The huts are adjacent to a tributary of the River Niger at a distance of 10 km from the Kainji Dam site and face rice fields known to harbor permanent mosquito breeding sites. The mosquitoes endemic to this area of Nigeria are highly endophillic, that is, they rest mainly indoors.

Human volunteers that participated as sleepers in this field trial were provided with anti-malarial chemical prophylaxis on a weekly basis, and the protocols used herein were reviewed and approved by the Research Ethics Review Committee of the Nigerian Institute of Medical Research. Six male adult volunteers, aged between 25 and 35 years old, were recruited to sleep in the huts described above. Sleepers were allocated to huts randomly for each series of trials, and this randomization process occurred nightly. The volunteers entered the huts by 21:00 each night and remained inside the huts until 06:30 the following morning. Each morning, the windows were closed and the exit traps blocked with a piece of cloth to prevent mosquitoes that entered from exiting. The traps were then put in a freezer at −20° C. to kill all the mosquitoes before being emptied for identification. By means of a sucking aspirator the verandas and rooms were visually searched for live mosquitoes and any insects found were collected in labelled cups. A 10-minute search was conducted for each but (room and veranda traps). The exit traps were emptied into a labelled cup and all the mosquitoes placed in the freezer at −20° C. for about 30 minutes before morphological identification.

The Mosquito Magnet trap Model-X (MM-X trap made by the firm formerly known as American Biophysics (ABC), USA) is a 12V battery operated counter-flow trap that was used as the repellent dispersing device to evaluate the efficacy of repellent compounds or compositions disclosed herein. Four compounds, carvacrol, cumin alcohol, ethyl cinnamate, and butyl cinnamate, were evaluated in comparison to DEET as a nonproprietary conventional repellent in a first experiment. The chemical compounds were provided in liquid form: carvacrol (98%), butyl cinnamate (98%), ethyl cinnamate (98%), cumin alcohol (97%) and DEET (97%). 1 ml of each compound was introduced into a 2.5 ml open vial of 1.2 cm diameter. This resulted in a surface area of 1.13 $cm^2$ in the vial. Each vial was then clipped onto a string and placed in the central MM-X trap compartment. A second experiment compared the effect of combination of two compounds, each MM-X trap contained 2 vials, each with a single chemical (0.5 ml volume). A but with a sleeper with an MM-X trap baited with human odour from a nylon sock was used as control.

The trap was hung 20 cm above the but floor inside the but near the mattress of each but with a human volunteer sleeping in the hut. Traps were switched on by 21:00 each evening to allow for product release and removed each morning by 06:30. New vials were prepared for each day. The experiment was designed using Latin Square approach with randomization based on 6 huts×12 nights array that was balanced to control for any carry over effect of treatments. Spatial repellent effects of products were assessed based on mosquito counts in the exit traps (ExTr in FIGS. 3 and 4; i.e. induced exophily), counts on the walls inside the huts and in the MM-X traps. Numbers of mosquitoes captured in window exit traps were compared in each experiment using a generalized linear model with a quasibinomial response followed by a Post-hoc Tukey test (in R V3.0.1). Findings were checked for carry-over effects of a product tested within a but the night before.

The 144 hut-night collections (24 nights×6 huts) yielded 1466 (38%) *Anopheles* spp., 2231 (53%) *Culex* spp. while the remaining was *Mansonia* spp. The *Anopheles* population showed a predominance of *Anopheles gambiae* s.l. consisting of 85% *Anopheles gambiae* s.s and 15% *Anopheles arabiensis*.

Figure 3:
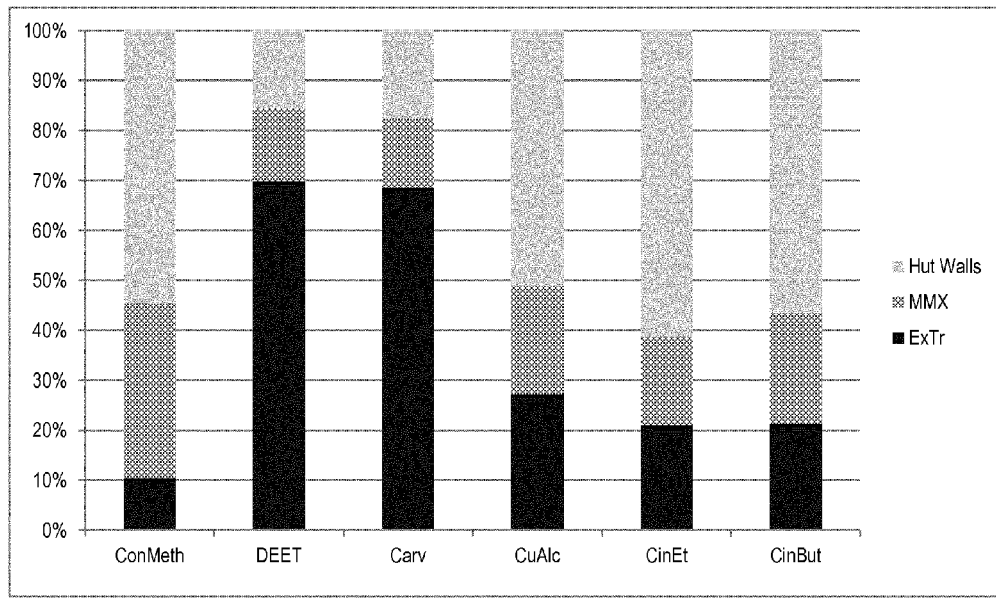
(FIG. 3 A) and *Culex* spp.
Figure 3:
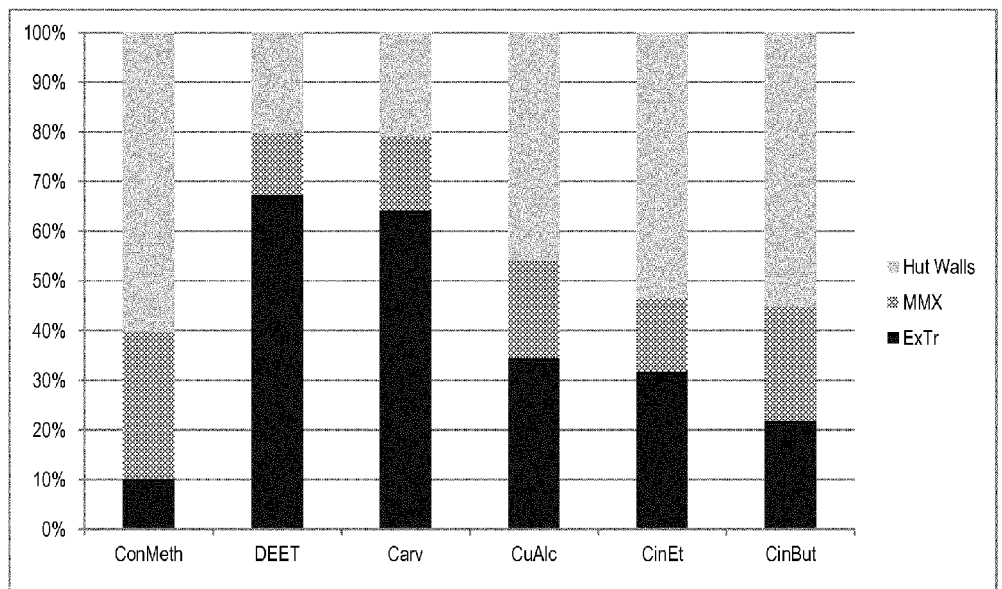
Figure 4:
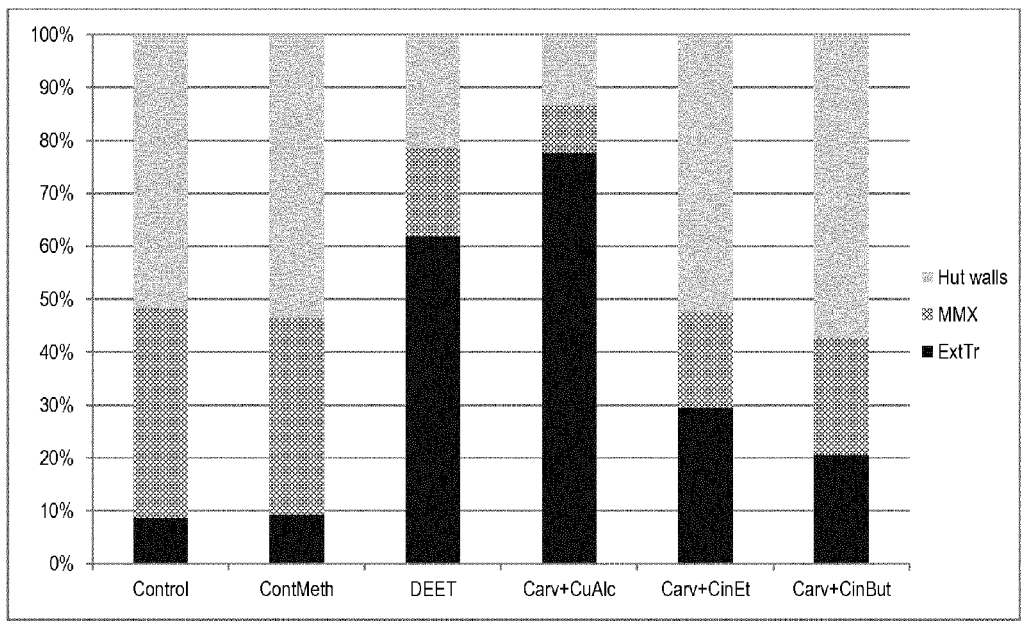
FIGS. 4A and 4B are as FIGS. 3A and 3B, but instead of individual compounds binary composition were tested to compare to DEET.
Figure 4:
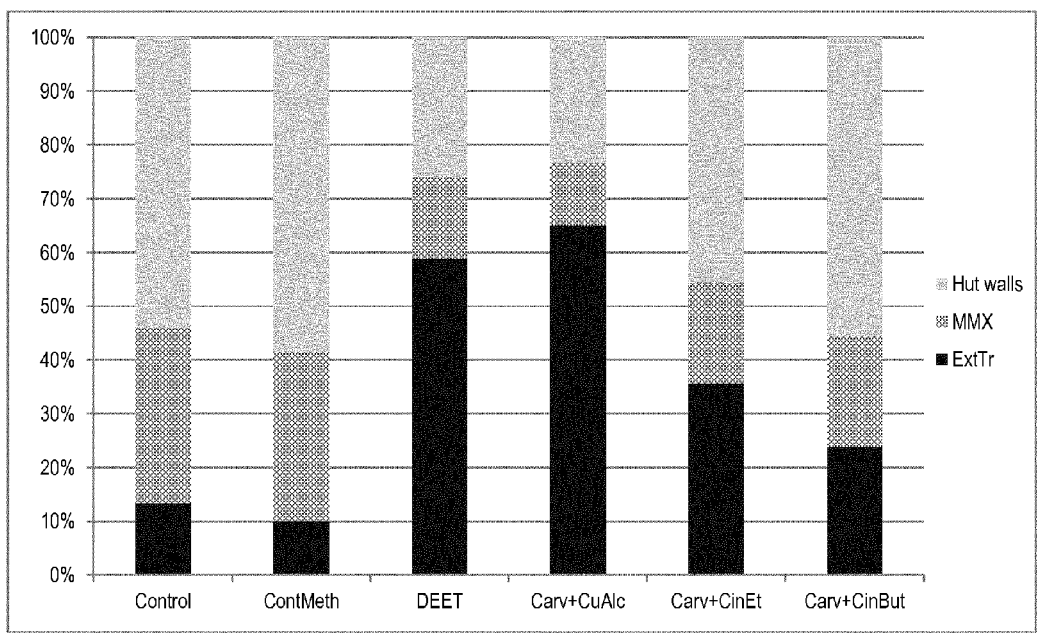

The spatial repellent effect of each product was expressed as the percentage of mosquitoes counted in the exit traps (induced exophily), on the walls and in the trap (FIGS. 3 and 4). Carvacrol had a spatial repellent effect similar to that of DEET ($P>0.05$) and significantly higher in terms of induced exophily on *Anopheles* spp. and *Culex* spp. than cumin alcohol, ethyl-cinnamate, butyl-cinnamate and the control ($P<0.001$; FIGS. 3A and 3B). The repellent effect of cumin alcohol, ethyl-cinnamate, butyl-cinnamate was significantly lower than that of DEET ($P<0.001$; FIGS. 3A and 3B). The induced exophily resulted in reduced mosquito counts on the inside walls of the huts for carvacrol and DEET, much lower than on the walls in the huts with cumin alcohol, ethyl-cinnamate, butyl-cinnamate and the control (FIGS. 3A and 3B).

Based on the above results and those presented in Example 7, the possible additive effects of combinations of compounds were tested. The traps were set up with combinations of carvacrol+cumin alcohol, carvacrol+ethyl-cinnamate and carvacrol+butyl-cinnamete compared to DEET (positive control). MM-X traps baited with methanol and empty traps were used as negative controls (FIGS. 4A and 4B). The experiment was again designed using the Latin Square design with randomization based on product×hut×night as indicated above.

The binary combination of carvacrol+cumin alcohol produced the highest repellent effect in terms of induced exophily on *Anopheles* and *Culex* spp. compared to the other binary combinations ($P<0.05$; FIGS. 4A and 4B), but was not different to DEET ($P>0.05$).

The described spatial repellent effects were achieved with release rates of approximately 1-10 mg amounts of products per night. Effects of the spatial repellents on *Culex* spp. were similar to those recorded for *Anopheles* spp., as can be seen by comparing FIG. 3A with FIG. 3B and FIG. 4A with FIG. 4B.

Example 10

Effects of Repellent Compounds on Other Blood-Feeding Arthropods—Sand Flies

To test the effects of repellent compounds or compositions disclosed herein on other blood-feeding arthropods, a warm body repellence assay (Kröber et. al. (2010). An In Vitro Assay for Testing Mosquito Repellents Employing a Warm Body and Carbon Dioxide as a Behavioral Activator. *Journal of the American Mosquito Control Association* 26(4): 381-386] was conducted using the sand fly *Lutzomyia longipalpis* (Diptera: Psychodidae), the principal vector of *Leishmania* (or leismaniasis) in the Americas.

To conduct a repellence assay with the sand fly, pure compounds or ethanol as negative control were applied to the warm body at a dose of about 3.8 μg/cm2 and tested for 2 minutes as described in Example 6. Fifty *L. longipalpis* sandflies (male:female ratio 1:1) of 3-7 days old were tested during the scotophase under conditions described for *A. gambiae* in Example 6. The test cages were lined with filter paper. Reduction in the number of landings by *L. longipalpis* sand fly females on a warm body treated with different test products compared to the control with solvent (ethanol p.a.) alone was used to evaluate repellence. Tests were conducted in complete darkness using IR LEDs to illuminate the warm body. Landings counted during 2 minutes were normalized by experimental day, cage, and number of females by a mixed linear model before testing for differences. Carvacrol and cuminic acid presented at 20 and 200 $nmol/cm^2$ were as effective as DEET at 20 $nmol/cm^2$ at repelling *L. longipalpis* sand flies from the warm body (Table 10).

TABLE 10

Repellent effect of candidate compounds on *L. longipalpis* compared to DEET

| Test product | Concentration ($nmol/cm^2$) | Median of landings | Difference to DEET at 20 $nmol/cm^2$ |
|---|---|---|---|
| Control | — | 48 | *** |
| DEET | 20 | 6 | Reference level |
|  | 200 | 5 | ns |

TABLE 10-continued

Repellent effect of candidate compounds on *L. longipalpis* compared to DEET

| Test product | Concentration (nmol/cm²) | Median of landings | Difference to DEET at 20 nmol/cm² |
|---|---|---|---|
| butyl cinnamate | 20 | 49 | *** |
|  | 200 | 40 | * |
| carvacrol | 20 | 23 | ns |
|  | 200 | 1 | ns |
| cuminic acid | 20 | 16 | ns |
|  | 200 | 13 | ns |

* $P \leq 0.1$;
** $P \leq 0.01$;
*** $P \leq 0.001$;
ns, not significantly different to DEET Example 11

Effects of Repellent Compounds on Other Blood-Feeding Arthropods—Ticks

The products were tested at a dose of 10 µg/cm² on *Ixodes ricinus* (Ixodidae) nymphs according the protocol described in Kröber, T. et al. (2013). A standardised in vivo and in vitro test method for evaluating tick repellents. *Pesticide Biochemistry and Physiology* 107: 160-168] with the following modifications: The test products (dissolved in ethanol) were allowed to evaporate for 40 s (as in the warm body test with mosquitoes) and the warm glass plates were used up to 250 s after application of the test products for the repellence assay. Four repetitions were made with carvacrol with 3, 4, 4 and 5 nymphs, i.e. with a total of 16 *I. ricinus* nymphs, of which in total 75% (12) were affected in that they either dropped off or walked down the warm glass plate.

The mixture of carvacrol+cumin alcohol+butyl-cinnamate was tested in two repetitions with 6 and 7 nymphs, i.e. with a total of 13 *I. ricinus* nymphs, of which 100% were affected in that they either dropped off or walked down the warm glass plate. Of 12 *Ixodes ricinus* tested in the control (ethanol only) only one tick (8%) was affected.

|  | % affected ticks |
|---|---|
| control | 8 |
| carvacrol | 75 |
| carvacrol + cuminic alcohol + butyl cinnamate | 100 |

CONCLUDING REMARKS

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of repelling an insect and/or an arachnid, the method consisting essentially of applying a composition to an animal, a human, a substrate and/or a location, the composition consisting essentially of an insect repelling amount and/or an arachnid repelling amount of a carvacrol compound, an insect repelling amount and/or an arachnid repelling amount of a cumin compound and an insect repelling amount and/or an arachnid repelling amount of a cinnamate compound, wherein the carvacrol compound is carvacrol, thymol or combinations thereof, the cumin compound is cumin alcohol, cuminic acid or combinations thereof; and the cinnamate compound is methyl cinnamate, ethyl cinnamate, butyl cinnamate, isobutyl cinnamate, N-butyl cinnamate, isopropyl cinnamate, E-cinnamyl acetate, cinnamaldehyde, E-cinnamaldehyde, Z-cinnamaldehyde, methoxycinnamaldehyde or combinations thereof, wherein application of the composition to the animal, the human, the substrate and/or the location repels the blood-feeding arthropod from the animal, the human, the substrate and/or the location.

2. The method according to claim 1, wherein application of the composition is by topical administration.

3. The method according to claim 1, wherein the insect is a blood-feeding insect.

4. The method according to claim 3, wherein the blood-feeding insect is a mosquito or sand fly.

5. The method according to claim 1, wherein the arachnid is a blood-feeding arachnid.

6. The method according to claim 5, wherein the blood-feeding arachnid is a tick.

7. The method according to claim 1, wherein the location is a plant or group of plants, a particular area of land, or a man-made structure.

8. The method according to claim 7, wherein the man-made structure is a commercial building, a house, a shed, a livestock maintenance area, other physical structure, or any part thereof.

9. A method of reducing bites of a blood-feeding arthropod in an animal or a human, the method consisting essentially of applying a composition to the animal or the human, the composition consisting essentially of a blood-feeding arthropod repelling amount of a carvacrol compound, a blood-feeding arthropod repelling amount of a cumin compound and a blood-feeding arthropod repelling amount of a cinnamate compound, wherein the carvacrol compound is carvacrol, thymol or combinations thereof, the cumin compound is cumin alcohol, cuminic acid or combinations thereof; and the cinnamate compound is methyl cinnamate, ethyl cinnamate, butyl cinnamate, isobutyl cinnamate, N-butyl cinnamate, isopropyl cinnamate, E-cinnamyl acetate, cinnamaldehyde, E-cinnamaldehyde, Z-cinnamaldehyde, methoxycinnamaldehyde or combinations thereof, wherein application of the composition repels the blood-feeding arthropod from the animal or the human, thereby reducing bites of blood-feeding arthropods.

10. The method according to claim 9, wherein application of the composition is by topical administration.

11. The method according to claim 10, wherein the blood-feeding arthropod is a blood-feeding insect or a blood-feeding arachnid.

12. The method according to claim 11, wherein the blood-feeding insect is a mosquito or sand fly.

13. The method according to claim 11, wherein the blood-feeding arachnid is a tick.

14. A method of reducing an infestation of a blood-feeding arthropod in a location, the method consisting essentially of applying a composition to the location, the composition consisting essentially of a blood-feeding arthropod repelling amount of a carvacrol compound, a blood-feeding arthropod repelling amount of a cumin compound and a blood-feeding arthropod repelling amount of a cinnamate compound, wherein the carvacrol compound is carvacrol, thymol or combinations thereof, the cumin compound is cumin alcohol, cuminic acid or combinations thereof; and the cinnamate compound is methyl cinnamate, ethyl cinnamate, butyl cinnamate, isobutyl cinnamate, N-butyl cinnamate, isopropyl cinnamate, E-cinnamyl acetate, cinnamaldehyde, E-cinnamaldehyde, Z-cinnamaldehyde, methoxycinnamaldehyde or combinations thereof wherein application of the composition to the location repels the blood-feeding arthropod from the location, thereby reducing the infestation.

15. The method according to claim 14, wherein application of the composition is by spraying.

16. The method according to claim 14, wherein the blood-feeding arthropod is a blood-feeding insect or a blood-feeding arachnid.

17. The method according to claim 16, wherein the blood-feeding insect is a mosquito or sand fly.

18. The method according to claim 16, wherein the blood-feeding arachnid is a tick.

19. The method according to claim 14, wherein the location is a plant or group of plants, a particular area of land, or a man-made structure.

20. The method according to claim 19, wherein the man-made structure is a commercial building, a house, a shed, a livestock maintenance area, other physical structure, or any part thereof.

* * * * *